US011904140B2

(12) United States Patent
Lee et al.

(10) Patent No.: US 11,904,140 B2
(45) Date of Patent: Feb. 20, 2024

(54) ADAPTABLE ASYMMETRIC MEDICAMENT COST COMPONENT IN A CONTROL SYSTEM FOR MEDICAMENT DELIVERY

(71) Applicant: Insulet Corporation, Acton, MA (US)

(72) Inventors: Joon Bok Lee, Acton, MA (US); Yibin Zheng, Hartland, WI (US); Jason O'Connor, Acton, MA (US); Trang Ly, Concord, MA (US)

(73) Assignee: INSULET CORPORATION, Acton, MA (US)

( * ) Notice: Subject to any disclaimer, the term of this patent is extended or adjusted under 35 U.S.C. 154(b) by 402 days.

(21) Appl. No.: 17/330,115

(22) Filed: May 25, 2021

(65) Prior Publication Data

US 2022/0288300 A1 Sep. 15, 2022

Related U.S. Application Data

(60) Provisional application No. 63/165,252, filed on Mar. 24, 2021, provisional application No. 63/158,918, filed on Mar. 10, 2021.

(51) Int. Cl.
*A61M 5/172* (2006.01)
*G16H 20/17* (2018.01)
(Continued)

(52) U.S. Cl.
CPC ....... *A61M 5/1723* (2013.01); *A61B 5/14532* (2013.01); *A61B 5/4839* (2013.01);
(Continued)

(58) Field of Classification Search
None
See application file for complete search history.

(56) References Cited

U.S. PATENT DOCUMENTS 303,013 A 8/1884 Horton
2,797,149 A 6/1957 Skeggs
(Continued)

FOREIGN PATENT DOCUMENTS

AU 2015200834 A1 3/2015
AU 2015301146 A1 3/2017
(Continued)

OTHER PUBLICATIONS

US 5,954,699 A, 09/1999, Jost et al. (withdrawn)
(Continued)

*Primary Examiner* — Manuel A Mendez
(74) *Attorney, Agent, or Firm* — GOODWIN PROCTER LLP

(57) ABSTRACT

The exemplary embodiments provide medicament delivery devices that use cost functions in their control systems to determine medicament dosages. The cost function may have a medicament cost component and a performance cost component. The exemplary embodiments may use cost functions having medicament cost components that scale asymmetrically for different ranges of inputs (i.e., different candidate medicament dosages). The variance in scaling for different input ranges provides added flexibility to tailor the medicament cost component to the user and thus provide better management of medicament delivery to the user and better conformance to a performance target. The exemplary embodiments may use a cost function that has a medicament cost component (such as an insulin cost component) of zero for candidate dosages for a range of candidate dosages (e.g., below a reference dosage).

23 Claims, 10 Drawing Sheets

(51) Int. Cl.
*A61B 5/145* (2006.01)
*A61B 5/00* (2006.01)
*A61M 5/142* (2006.01)
*G06Q 30/0283* (2023.01)

(52) U.S. Cl.
CPC ......... *A61M 5/142* (2013.01); *G06Q 30/0283* (2013.01); *G16H 20/17* (2018.01); *A61M 2005/14208* (2013.01); *A61M 2205/52* (2013.01); *A61M 2230/201* (2013.01)

(56) References Cited

U.S. PATENT DOCUMENTS

| | | |
|---|---|---|
| 3,631,847 A | 1/1972 | Hobbs |
| 3,634,039 A | 1/1972 | Brondy |
| 3,812,843 A | 5/1974 | Wootten et al. |
| 3,841,328 A | 10/1974 | Jensen |
| 3,963,380 A | 6/1976 | Thomas, Jr. et al. |
| 4,055,175 A | 10/1977 | Clemens et al. |
| 4,146,029 A | 3/1979 | Ellinwood, Jr. |
| 4,151,845 A | 5/1979 | Clemens |
| 4,245,634 A | 1/1981 | Albisser et al. |
| 4,368,980 A | 1/1983 | Aldred et al. |
| 4,373,527 A | 2/1983 | Fischell |
| 4,403,984 A | 9/1983 | Ash et al. |
| 4,464,170 A | 8/1984 | Clemens et al. |
| 4,469,481 A | 9/1984 | Kobayashi |
| 4,475,901 A | 10/1984 | Kraegen et al. |
| 4,526,568 A | 7/1985 | Clemens et al. |
| 4,526,569 A | 7/1985 | Bernardi |
| 4,529,401 A | 7/1985 | Leslie et al. |
| 4,559,033 A | 12/1985 | Stephen et al. |
| 4,559,037 A | 12/1985 | Franetzki et al. |
| 4,573,968 A | 3/1986 | Parker |
| 4,624,661 A | 11/1986 | Arimond |
| 4,633,878 A | 1/1987 | Bombardieri |
| 4,657,529 A | 4/1987 | Prince et al. |
| 4,685,903 A | 8/1987 | Cable et al. |
| 4,731,726 A | 3/1988 | Allen, III |
| 4,743,243 A | 5/1988 | Vaillancourt |
| 4,755,173 A | 7/1988 | Konopka et al. |
| 4,781,688 A | 11/1988 | Thoma et al. |
| 4,781,693 A | 11/1988 | Martinez et al. |
| 4,808,161 A | 2/1989 | Kamen |
| 4,854,170 A | 8/1989 | Brimhall et al. |
| 4,886,499 A | 12/1989 | Cirelli et al. |
| 4,900,292 A | 2/1990 | Berry et al. |
| 4,919,596 A | 4/1990 | Slate et al. |
| 4,925,444 A | 5/1990 | Orkin et al. |
| 4,940,527 A | 7/1990 | Kazlauskas et al. |
| 4,975,581 A | 12/1990 | Robinson et al. |
| 4,976,720 A | 12/1990 | Machold et al. |
| 4,981,140 A | 1/1991 | Wyatt |
| 4,994,047 A | 2/1991 | Walker et al. |
| 5,007,286 A | 4/1991 | Malcolm et al. |
| 5,097,834 A | 3/1992 | Skrabal |
| 5,102,406 A | 4/1992 | Arnold |
| 5,109,850 A | 5/1992 | Blanco et al. |
| 5,125,415 A | 6/1992 | Bell |
| 5,134,079 A | 7/1992 | Cusack et al. |
| 5,153,827 A | 10/1992 | Coutre et al. |
| 5,165,406 A | 11/1992 | Wong |
| 5,176,662 A | 1/1993 | Bartholomew et al. |
| 5,178,609 A | 1/1993 | Ishikawa |
| 5,207,642 A | 5/1993 | Orkin et al. |
| 5,232,439 A | 8/1993 | Campbell et al. |
| 5,237,993 A | 8/1993 | Skrabal |
| 5,244,463 A | 9/1993 | Cordner, Jr. et al. |
| 5,257,980 A | 11/1993 | Van Antwerp et al. |
| 5,273,517 A | 12/1993 | Barone et al. |
| 5,281,808 A | 1/1994 | Kunkel |
| 5,299,571 A | 4/1994 | Mastrototaro |
| 5,308,982 A | 5/1994 | Ivaldi et al. |
| 5,342,298 A | 8/1994 | Michaels et al. |
| 5,377,674 A | 1/1995 | Kuestner |
| 5,380,665 A | 1/1995 | Cusack et al. |
| 5,385,539 A | 1/1995 | Maynard |
| 5,389,078 A | 2/1995 | Zalesky |
| 5,411,889 A | 5/1995 | Hoots et al. |
| 5,421,812 A | 6/1995 | Langley et al. |
| 5,468,727 A | 11/1995 | Phillips et al. |
| 5,505,709 A | 4/1996 | Funderburk et al. |
| 5,505,828 A | 4/1996 | Wong et al. |
| 5,507,288 A | 4/1996 | Bocker et al. |
| 5,533,389 A | 7/1996 | Kamen et al. |
| 5,558,640 A | 9/1996 | Pfeiler et al. |
| 5,569,186 A | 10/1996 | Lord et al. |
| 5,584,813 A | 12/1996 | Livingston et al. |
| 5,609,572 A | 3/1997 | Lang |
| 5,665,065 A | 9/1997 | Colman et al. |
| 5,678,539 A | 10/1997 | Schubert et al. |
| 5,685,844 A | 11/1997 | Marttila |
| 5,685,859 A | 11/1997 | Kornerup |
| 5,693,018 A | 12/1997 | Kriesel et al. |
| 5,697,899 A | 12/1997 | Hillman et al. |
| 5,700,695 A | 12/1997 | Yassinzadeh et al. |
| 5,703,364 A | 12/1997 | Rosenthal |
| 5,714,123 A | 2/1998 | Sohrab |
| 5,716,343 A | 2/1998 | Kriesel et al. |
| 5,722,397 A | 3/1998 | Eppstein |
| 5,741,228 A | 4/1998 | Lambrecht et al. |
| 5,746,217 A | 5/1998 | Erickson et al. |
| 5,755,682 A | 5/1998 | Knudson et al. |
| 5,758,643 A | 6/1998 | Wong et al. |
| 5,800,405 A | 9/1998 | McPhee |
| 5,800,420 A | 9/1998 | Gross et al. |
| 5,801,057 A | 9/1998 | Smart et al. |
| 5,804,048 A | 9/1998 | Wong et al. |
| 5,817,007 A | 10/1998 | Fodgaard et al. |
| 5,820,622 A | 10/1998 | Gross et al. |
| 5,823,951 A | 10/1998 | Messerschmidt |
| 5,840,020 A | 11/1998 | Heinonen et al. |
| 5,848,991 A | 12/1998 | Gross et al. |
| 5,851,197 A | 12/1998 | Marano et al. |
| 5,858,005 A | 1/1999 | Kriesel |
| 5,865,806 A | 2/1999 | Howell |
| 5,871,470 A | 2/1999 | McWha |
| 5,879,310 A | 3/1999 | Sopp et al. |
| 5,902,253 A | 5/1999 | Pfeiffer et al. |
| 5,931,814 A | 8/1999 | Alex et al. |
| 5,932,175 A | 8/1999 | Knute et al. |
| 5,935,099 A | 8/1999 | Peterson et al. |
| 5,947,911 A | 9/1999 | Wong et al. |
| 5,971,941 A | 10/1999 | Simons et al. |
| 5,993,423 A | 11/1999 | Choi |
| 5,997,501 A | 12/1999 | Gross et al. |
| 6,017,318 A | 1/2000 | Gauthier et al. |
| 6,024,539 A | 2/2000 | Blomquist |
| 6,032,059 A | 2/2000 | Henning et al. |
| 6,036,924 A | 3/2000 | Simons et al. |
| 6,040,578 A | 3/2000 | Malin et al. |
| 6,049,727 A | 4/2000 | Crothall |
| 6,050,978 A | 4/2000 | Orr et al. |
| 6,058,934 A | 5/2000 | Sullivan |
| 6,066,103 A | 5/2000 | Duchon et al. |
| 6,071,292 A | 6/2000 | Makower et al. |
| 6,072,180 A | 6/2000 | Kramer et al. |
| 6,077,055 A | 6/2000 | Vilks |
| 6,090,092 A | 7/2000 | Fowles et al. |
| 6,101,406 A | 8/2000 | Hacker et al. |
| 6,102,872 A | 8/2000 | Doneen et al. |
| 6,115,673 A | 9/2000 | Malin et al. |
| 6,123,827 A | 9/2000 | Wong et al. |
| 6,124,134 A | 9/2000 | Stark |
| 6,126,637 A | 10/2000 | Kriesel et al. |
| 6,128,519 A | 10/2000 | Say |
| 6,142,939 A | 11/2000 | Eppstein et al. |
| 6,143,164 A | 11/2000 | Heller et al. |
| 6,157,041 A | 12/2000 | Thomas et al. |
| 6,161,028 A | 12/2000 | Braig et al. |
| 6,162,639 A | 12/2000 | Douglas |
| 6,196,046 B1 | 3/2001 | Braig et al. |
| 6,200,287 B1 | 3/2001 | Keller et al. |
| 6,200,338 B1 | 3/2001 | Solomon et al. |

(56) References Cited

U.S. PATENT DOCUMENTS

| | | |
|---|---|---|
| 6,214,629 B1 | 4/2001 | Freitag et al. |
| 6,226,082 B1 | 5/2001 | Roe |
| 6,244,776 B1 | 6/2001 | Wiley |
| 6,261,065 B1 | 7/2001 | Nayak et al. |
| 6,262,798 B1 | 7/2001 | Shepherd et al. |
| 6,270,455 B1 | 8/2001 | Brown |
| 6,271,045 B1 | 8/2001 | Douglas et al. |
| 6,280,381 B1 | 8/2001 | Malin et al. |
| 6,285,448 B1 | 9/2001 | Kuenstner |
| 6,309,370 B1 | 10/2001 | Haim et al. |
| 6,312,888 B1 | 11/2001 | Wong et al. |
| 6,334,851 B1 | 1/2002 | Hayes et al. |
| 6,375,627 B1 | 4/2002 | Mauze et al. |
| 6,379,301 B1 | 4/2002 | Worthington et al. |
| 6,402,689 B1 | 6/2002 | Scarantino et al. |
| 6,470,279 B1 | 10/2002 | Samsoondar |
| 6,475,196 B1 | 11/2002 | Vachon |
| 6,477,901 B1 | 11/2002 | Tadigadapa et al. |
| 6,484,044 B1 | 11/2002 | Lilienfeld-Toal |
| 6,491,656 B1 | 12/2002 | Morris |
| 6,512,937 B2 | 1/2003 | Blank et al. |
| 6,525,509 B1 | 2/2003 | Petersson et al. |
| 6,528,809 B1 | 3/2003 | Thomas et al. |
| 6,540,672 B1 | 4/2003 | Simonsen et al. |
| 6,544,212 B2 | 4/2003 | Galley et al. |
| 6,546,268 B1 | 4/2003 | Ishikawa et al. |
| 6,546,269 B1 | 4/2003 | Kurnik |
| 6,553,841 B1 | 4/2003 | Blouch |
| 6,554,798 B1 | 4/2003 | Mann et al. |
| 6,556,850 B1 | 4/2003 | Braig et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,562,014 B2 | 5/2003 | Lin et al. |
| 6,569,125 B2 | 5/2003 | Jepson et al. |
| 6,572,542 B1 | 6/2003 | Houben et al. |
| 6,572,545 B2 | 6/2003 | Knobbe et al. |
| 6,574,490 B2 | 6/2003 | Abbink et al. |
| 6,575,905 B2 | 6/2003 | Knobbe et al. |
| 6,580,934 B1 | 6/2003 | Braig et al. |
| 6,618,603 B2 | 9/2003 | Varalli et al. |
| 6,633,772 B2 | 10/2003 | Ford et al. |
| 6,645,142 B2 | 11/2003 | Braig et al. |
| 6,653,091 B1 | 11/2003 | Dunn et al. |
| 6,662,030 B2 | 12/2003 | Khalil et al. |
| 6,669,663 B1 | 12/2003 | Thompson |
| 6,678,542 B2 | 1/2004 | Braig et al. |
| 6,699,221 B2 | 3/2004 | Vaillancourt |
| 6,718,189 B2 | 4/2004 | Rohrscheib et al. |
| 6,721,582 B2 | 4/2004 | Trepagnier et al. |
| 6,728,560 B2 | 4/2004 | Kollias et al. |
| 6,740,059 B2 | 5/2004 | Flaherty |
| 6,740,072 B2 | 5/2004 | Starkweather et al. |
| 6,751,490 B2 | 6/2004 | Esenaliev et al. |
| 6,758,835 B2 | 7/2004 | Close et al. |
| 6,780,156 B2 | 8/2004 | Haueter et al. |
| 6,810,290 B2 | 10/2004 | Lebel et al. |
| 6,837,858 B2 | 1/2005 | Cunningham et al. |
| 6,837,988 B2 | 1/2005 | Leong et al. |
| 6,846,288 B2 | 1/2005 | Nagar et al. |
| 6,862,534 B2 | 3/2005 | Sterling et al. |
| 6,865,408 B1 | 3/2005 | Abbink et al. |
| 6,890,291 B2 | 5/2005 | Robinson et al. |
| 6,936,029 B2 | 8/2005 | Mann et al. |
| 6,949,081 B1 | 9/2005 | Chance |
| 6,958,809 B2 | 10/2005 | Sterling et al. |
| 6,989,891 B2 | 1/2006 | Braig et al. |
| 6,990,366 B2 | 1/2006 | Say et al. |
| 7,008,404 B2 | 3/2006 | Nakajima |
| 7,009,180 B2 | 3/2006 | Sterling et al. |
| 7,016,713 B2 | 3/2006 | Gardner et al. |
| 7,018,360 B2 | 3/2006 | Flaherty et al. |
| 7,025,743 B2 | 4/2006 | Mann et al. |
| 7,025,744 B2 | 4/2006 | Utterberg et al. |
| 7,027,848 B2 | 4/2006 | Robinson et al. |
| 7,043,288 B2 | 5/2006 | Davis, III et al. |
| 7,060,059 B2 | 6/2006 | Keith et al. |
| 7,061,593 B2 | 6/2006 | Braig et al. |
| 7,096,124 B2 | 8/2006 | Sterling et al. |
| 7,115,205 B2 | 10/2006 | Robinson et al. |
| 7,128,727 B2 | 10/2006 | Flaherty et al. |
| 7,139,593 B2 | 11/2006 | Kavak et al. |
| 7,139,598 B2 | 11/2006 | Hull et al. |
| 7,144,384 B2 | 12/2006 | Gorman et al. |
| 7,171,252 B1 | 1/2007 | Scarantino et al. |
| 7,190,988 B2 | 3/2007 | Say et al. |
| 7,204,823 B2 | 4/2007 | Estes et al. |
| 7,248,912 B2 | 7/2007 | Gough et al. |
| 7,267,665 B2 | 9/2007 | Steil et al. |
| 7,271,912 B2 | 9/2007 | Sterling et al. |
| 7,278,983 B2 | 10/2007 | Ireland et al. |
| 7,291,107 B2 | 11/2007 | Hellwig et al. |
| 7,291,497 B2 | 11/2007 | Holmes et al. |
| 7,303,549 B2 | 12/2007 | Flaherty et al. |
| 7,303,622 B2 | 12/2007 | Loch et al. |
| 7,303,922 B2 | 12/2007 | Jeng et al. |
| 7,354,420 B2 | 4/2008 | Steil et al. |
| 7,388,202 B2 | 6/2008 | Sterling et al. |
| 7,402,153 B2 | 7/2008 | Steil et al. |
| 7,404,796 B2 | 7/2008 | Ginsberg |
| 7,429,255 B2 | 9/2008 | Thompson |
| 7,460,130 B2 | 12/2008 | Salganicoff |
| 7,481,787 B2 | 1/2009 | Gable et al. |
| 7,491,187 B2 | 2/2009 | Van Den Berghe et al. |
| 7,500,949 B2 | 3/2009 | Gottlieb et al. |
| 7,509,156 B2 | 3/2009 | Flanders |
| 7,547,281 B2 | 6/2009 | Hayes et al. |
| 7,569,030 B2 | 8/2009 | Lebel et al. |
| 7,608,042 B2 | 10/2009 | Goldberger et al. |
| 7,651,845 B2 | 1/2010 | Doyle, III et al. |
| 7,680,529 B2 | 3/2010 | Kroll |
| 7,734,323 B2 | 6/2010 | Blomquist et al. |
| 7,766,829 B2 | 8/2010 | Sloan et al. |
| 7,785,258 B2 | 8/2010 | Braig et al. |
| 7,806,854 B2 | 10/2010 | Damiano et al. |
| 7,806,886 B2 | 10/2010 | Kanderian, Jr. et al. |
| 7,918,825 B2 | 4/2011 | OConnor et al. |
| 7,946,985 B2 | 5/2011 | Mastrototaro et al. |
| 7,972,296 B2 | 7/2011 | Braig et al. |
| 8,221,345 B2 | 7/2012 | Blomquist |
| 8,251,907 B2 | 8/2012 | Sterling et al. |
| 8,449,524 B2 | 5/2013 | Braig et al. |
| 8,452,359 B2 | 5/2013 | Rebec et al. |
| 8,454,576 B2 | 6/2013 | Mastrototaro et al. |
| 8,467,980 B2 | 6/2013 | Campbell et al. |
| 8,478,557 B2 | 7/2013 | Hayter et al. |
| 8,547,239 B2 | 10/2013 | Peatfield et al. |
| 8,597,274 B2 | 12/2013 | Sloan et al. |
| 8,622,988 B2 | 1/2014 | Hayter |
| 8,810,394 B2 | 8/2014 | Kalpin |
| 9,061,097 B2 | 6/2015 | Holt et al. |
| 9,171,343 B1 | 10/2015 | Fischell et al. |
| 9,233,204 B2 | 1/2016 | Booth et al. |
| 9,486,571 B2 | 11/2016 | Rosinko |
| 9,579,456 B2 | 2/2017 | Budiman et al. |
| 9,743,224 B2 | 8/2017 | San Vicente et al. |
| 9,907,515 B2 | 3/2018 | Doyle, III et al. |
| 9,980,140 B1 | 5/2018 | Spencer et al. |
| 9,984,773 B2 | 5/2018 | Gondhalekar et al. |
| 10,248,839 B2 | 4/2019 | Levy et al. |
| 10,335,464 B1 | 7/2019 | Michelich et al. |
| 10,583,250 B2 | 3/2020 | Mazlish et al. |
| 10,737,024 B2 | 8/2020 | Schmid |
| 10,987,468 B2 | 4/2021 | Mazlish et al. |
| 11,197,964 B2 | 12/2021 | Sjolund et al. |
| 11,260,169 B2 | 3/2022 | Estes |
| 11,547,800 B2 * | 1/2023 | Lee ............... A61K 38/28 |
| 11,607,493 B2 * | 3/2023 | Lee ............... A61M 5/1723 |
| 2001/0021803 A1 | 9/2001 | Blank et al. |
| 2001/0034023 A1 | 10/2001 | Stanton, Jr. et al. |
| 2001/0034502 A1 | 10/2001 | Moberg et al. |
| 2001/0051377 A1 | 12/2001 | Hammer et al. |
| 2001/0053895 A1 | 12/2001 | Vaillancourt |

(56) References Cited

U.S. PATENT DOCUMENTS

| | | |
|---|---|---|
| 2002/0010401 A1 | 1/2002 | Bushmakin et al. |
| 2002/0010423 A1 | 1/2002 | Gross et al. |
| 2002/0016568 A1 | 2/2002 | Lebel et al. |
| 2002/0040208 A1 | 4/2002 | Flaherty et al. |
| 2002/0123740 A1 | 9/2002 | Flaherty et al. |
| 2002/0128543 A1 | 9/2002 | Leonhardt |
| 2002/0147423 A1 | 10/2002 | Burbank et al. |
| 2002/0155425 A1 | 10/2002 | Han et al. |
| 2002/0161288 A1 | 10/2002 | Shin et al. |
| 2003/0023148 A1 | 1/2003 | Lorenz et al. |
| 2003/0050621 A1 | 3/2003 | Lebel et al. |
| 2003/0060692 A1 | 3/2003 | Ruchti et al. |
| 2003/0086074 A1 | 5/2003 | Braig et al. |
| 2003/0086075 A1 | 5/2003 | Braig et al. |
| 2003/0090649 A1 | 5/2003 | Sterling et al. |
| 2003/0100040 A1 | 5/2003 | Bonnecaze et al. |
| 2003/0130616 A1 | 7/2003 | Steil et al. |
| 2003/0135388 A1 | 7/2003 | Martucci et al. |
| 2003/0144582 A1 | 7/2003 | Cohen et al. |
| 2003/0163097 A1 | 8/2003 | Fleury et al. |
| 2003/0195404 A1 | 10/2003 | Knobbe et al. |
| 2003/0208113 A1 | 11/2003 | Mault et al. |
| 2003/0208154 A1 | 11/2003 | Close et al. |
| 2003/0212379 A1 | 11/2003 | Bylund et al. |
| 2003/0216627 A1 | 11/2003 | Lorenz et al. |
| 2003/0220605 A1 | 11/2003 | Bowman, Jr. et al. |
| 2004/0010207 A1 | 1/2004 | Flaherty et al. |
| 2004/0034295 A1 | 2/2004 | Salganicoff |
| 2004/0045879 A1 | 3/2004 | Shults et al. |
| 2004/0051368 A1 | 3/2004 | Caputo et al. |
| 2004/0064259 A1 | 4/2004 | Haaland et al. |
| 2004/0097796 A1 | 5/2004 | Berman et al. |
| 2004/0116847 A1 | 6/2004 | Wall |
| 2004/0122353 A1 | 6/2004 | Shahmirian et al. |
| 2004/0133166 A1 | 7/2004 | Moberg et al. |
| 2004/0147034 A1 | 7/2004 | Gore et al. |
| 2004/0171983 A1 | 9/2004 | Sparks et al. |
| 2004/0203357 A1 | 10/2004 | Nassimi |
| 2004/0204868 A1 | 10/2004 | Maynard et al. |
| 2004/0215492 A1 | 10/2004 | Choi |
| 2004/0220517 A1 | 11/2004 | Starkweather et al. |
| 2004/0241736 A1 | 12/2004 | Hendee et al. |
| 2004/0249308 A1 | 12/2004 | Forssell |
| 2005/0003470 A1 | 1/2005 | Nelson et al. |
| 2005/0020980 A1 | 1/2005 | Inoue et al. |
| 2005/0022274 A1 | 1/2005 | Campbell et al. |
| 2005/0033148 A1 | 2/2005 | Haueter et al. |
| 2005/0049179 A1 | 3/2005 | Davidson et al. |
| 2005/0065464 A1 | 3/2005 | Talbot et al. |
| 2005/0065465 A1 | 3/2005 | Lebel et al. |
| 2005/0075624 A1 | 4/2005 | Miesel |
| 2005/0105095 A1 | 5/2005 | Pesach et al. |
| 2005/0137573 A1 | 6/2005 | Mclaughlin |
| 2005/0171503 A1 | 8/2005 | Van Den Berghe et al. |
| 2005/0182306 A1 | 8/2005 | Sloan |
| 2005/0192494 A1 | 9/2005 | Ginsberg |
| 2005/0192557 A1 | 9/2005 | Brauker et al. |
| 2005/0197621 A1 | 9/2005 | Poulsen et al. |
| 2005/0203360 A1 | 9/2005 | Brauker et al. |
| 2005/0203461 A1 | 9/2005 | Flaherty et al. |
| 2005/0238507 A1 | 10/2005 | Dilanni et al. |
| 2005/0261660 A1 | 11/2005 | Choi |
| 2005/0272640 A1 | 12/2005 | Doyle, III et al. |
| 2005/0277912 A1 | 12/2005 | John |
| 2006/0009727 A1 | 1/2006 | OMahony et al. |
| 2006/0079809 A1 | 4/2006 | Goldberger et al. |
| 2006/0100494 A1 | 5/2006 | Kroll |
| 2006/0134323 A1 | 6/2006 | OBrien |
| 2006/0167350 A1 | 7/2006 | Monfre et al. |
| 2006/0173406 A1 | 8/2006 | Hayes et al. |
| 2006/0189925 A1 | 8/2006 | Gable et al. |
| 2006/0189926 A1 | 8/2006 | Hall et al. |
| 2006/0197015 A1 | 9/2006 | Sterling et al. |
| 2006/0200070 A1 | 9/2006 | Callicoat et al. |
| 2006/0204535 A1 | 9/2006 | Johnson |
| 2006/0229531 A1 | 10/2006 | Goldberger et al. |
| 2006/0253085 A1 | 11/2006 | Geismar et al. |
| 2006/0264895 A1 | 11/2006 | Flanders |
| 2006/0270983 A1 | 11/2006 | Lord et al. |
| 2006/0276771 A1 | 12/2006 | Galley et al. |
| 2006/0282290 A1 | 12/2006 | Flaherty et al. |
| 2007/0016127 A1 | 1/2007 | Staib et al. |
| 2007/0060796 A1 | 3/2007 | Kim |
| 2007/0060869 A1 | 3/2007 | Tolle et al. |
| 2007/0060872 A1 | 3/2007 | Hall et al. |
| 2007/0083160 A1 | 4/2007 | Hall et al. |
| 2007/0106135 A1 | 5/2007 | Sloan et al. |
| 2007/0116601 A1 | 5/2007 | Patton |
| 2007/0118405 A1 | 5/2007 | Campbell et al. |
| 2007/0129690 A1 | 6/2007 | Rosenblatt et al. |
| 2007/0142720 A1 | 6/2007 | Ridder et al. |
| 2007/0173761 A1 | 7/2007 | Kanderian et al. |
| 2007/0173974 A1 | 7/2007 | Lin et al. |
| 2007/0179352 A1 | 8/2007 | Randlov et al. |
| 2007/0191716 A1 | 8/2007 | Goldberger et al. |
| 2007/0197163 A1 | 8/2007 | Robertson |
| 2007/0225675 A1 | 9/2007 | Robinson et al. |
| 2007/0244381 A1 | 10/2007 | Robinson et al. |
| 2007/0249007 A1 | 10/2007 | Rosero |
| 2007/0264707 A1 | 11/2007 | Liederman et al. |
| 2007/0282269 A1 | 12/2007 | Carter et al. |
| 2007/0287985 A1 | 12/2007 | Estes et al. |
| 2007/0293843 A1 | 12/2007 | Ireland et al. |
| 2008/0033272 A1 | 2/2008 | Gough et al. |
| 2008/0051764 A1 | 2/2008 | Dent et al. |
| 2008/0058625 A1 | 3/2008 | McGarraugh et al. |
| 2008/0065050 A1 | 3/2008 | Sparks et al. |
| 2008/0071157 A1 | 3/2008 | McGarraugh et al. |
| 2008/0071158 A1 | 3/2008 | McGarraugh et al. |
| 2008/0078400 A1 | 4/2008 | Martens et al. |
| 2008/0097289 A1 | 4/2008 | Steil et al. |
| 2008/0132880 A1 | 6/2008 | Buchman |
| 2008/0161664 A1 | 7/2008 | Mastrototaro et al. |
| 2008/0172026 A1 | 7/2008 | Blomquist |
| 2008/0177165 A1 | 7/2008 | Blomquist et al. |
| 2008/0188796 A1 | 8/2008 | Steil et al. |
| 2008/0200838 A1 | 8/2008 | Goldberger et al. |
| 2008/0206067 A1 | 8/2008 | De Corral et al. |
| 2008/0208113 A1 | 8/2008 | Damiano et al. |
| 2008/0214919 A1 | 9/2008 | Harmon et al. |
| 2008/0228056 A1 | 9/2008 | Blomquist et al. |
| 2008/0249386 A1 | 10/2008 | Besterman et al. |
| 2008/0269585 A1 | 10/2008 | Ginsberg |
| 2008/0269714 A1 | 10/2008 | Mastrototaro et al. |
| 2008/0269723 A1 | 10/2008 | Mastrototaro et al. |
| 2008/0287906 A1 | 11/2008 | Burkholz et al. |
| 2009/0006061 A1 | 1/2009 | Thukral et al. |
| 2009/0018406 A1 | 1/2009 | Yodfat et al. |
| 2009/0030398 A1 | 1/2009 | Yodfat et al. |
| 2009/0036753 A1 | 2/2009 | King |
| 2009/0043240 A1 | 2/2009 | Robinson et al. |
| 2009/0054753 A1 | 2/2009 | Robinson et al. |
| 2009/0069743 A1 | 3/2009 | Krishnamoorthy et al. |
| 2009/0069745 A1 | 3/2009 | Estes et al. |
| 2009/0069787 A1 | 3/2009 | Estes et al. |
| 2009/0099521 A1 | 4/2009 | Gravesen et al. |
| 2009/0105573 A1 | 4/2009 | Malecha |
| 2009/0131861 A1 | 5/2009 | Braig et al. |
| 2009/0156922 A1 | 6/2009 | Goldberger et al. |
| 2009/0156924 A1 | 6/2009 | Shariati et al. |
| 2009/0163781 A1 | 6/2009 | Say et al. |
| 2009/0198350 A1 | 8/2009 | Thiele |
| 2009/0221890 A1 | 9/2009 | Saffer et al. |
| 2009/0228214 A1 | 9/2009 | Say et al. |
| 2009/0318791 A1 | 12/2009 | Kaastrup |
| 2009/0326343 A1 | 12/2009 | Gable et al. |
| 2010/0057042 A1 | 3/2010 | Hayter |
| 2010/0114026 A1 | 5/2010 | Karratt et al. |
| 2010/0121170 A1 | 5/2010 | Rule |
| 2010/0137784 A1 | 6/2010 | Cefai et al. |
| 2010/0152658 A1 | 6/2010 | Hanson et al. |
| 2010/0174228 A1 | 7/2010 | Buckingham et al. |
| 2010/0211003 A1 | 8/2010 | Sundar et al. |
| 2010/0228110 A1 | 9/2010 | Tsoukalis |

(56) References Cited

U.S. PATENT DOCUMENTS

| | | |
|---|---|---|
| 2010/0262117 A1 | 10/2010 | Magni et al. |
| 2010/0262434 A1 | 10/2010 | Shaya |
| 2010/0295686 A1 | 11/2010 | Sloan et al. |
| 2010/0298765 A1 | 11/2010 | Budiman et al. |
| 2011/0021584 A1 | 1/2011 | Berggren et al. |
| 2011/0028817 A1 | 2/2011 | Jin et al. |
| 2011/0054390 A1 | 3/2011 | Searle et al. |
| 2011/0054399 A1 | 3/2011 | Chong et al. |
| 2011/0124996 A1 | 5/2011 | Reinke et al. |
| 2011/0144586 A1 | 6/2011 | Michaud et al. |
| 2011/0160652 A1 | 6/2011 | Yodfat et al. |
| 2011/0178472 A1 | 7/2011 | Cabiri |
| 2011/0190694 A1 | 8/2011 | Lanier, Jr. et al. |
| 2011/0202005 A1 | 8/2011 | Yodfat et al. |
| 2011/0218495 A1 | 9/2011 | Remde |
| 2011/0230833 A1 | 9/2011 | Landman et al. |
| 2011/0251509 A1 | 10/2011 | Beyhan et al. |
| 2011/0313680 A1 | 12/2011 | Doyle et al. |
| 2011/0316562 A1 | 12/2011 | Cefai et al. |
| 2012/0003935 A1 | 1/2012 | Lydon et al. |
| 2012/0010594 A1 | 1/2012 | Holt et al. |
| 2012/0030393 A1 | 2/2012 | Ganesh et al. |
| 2012/0053556 A1 | 3/2012 | Lee |
| 2012/0078067 A1 | 3/2012 | Kovatchev et al. |
| 2012/0078161 A1 | 3/2012 | Masterson et al. |
| 2012/0078181 A1 | 3/2012 | Smith et al. |
| 2012/0101451 A1 | 4/2012 | Boit et al. |
| 2012/0123234 A1 | 5/2012 | Atlas et al. |
| 2012/0136336 A1 | 5/2012 | Mastrototaro et al. |
| 2012/0190955 A1 | 7/2012 | Rao et al. |
| 2012/0203085 A1 | 8/2012 | Rebec |
| 2012/0203178 A1 | 8/2012 | Tverskoy |
| 2012/0215087 A1 | 8/2012 | Cobelli et al. |
| 2012/0225134 A1 | 9/2012 | Komorowski |
| 2012/0226259 A1 | 9/2012 | Yodfat et al. |
| 2012/0232520 A1 | 9/2012 | Sloan et al. |
| 2012/0238851 A1 | 9/2012 | Kamen et al. |
| 2012/0271655 A1 | 10/2012 | Knobel et al. |
| 2012/0277668 A1 | 11/2012 | Chawla |
| 2012/0282111 A1 | 11/2012 | Nip et al. |
| 2012/0295550 A1 | 11/2012 | Wilson et al. |
| 2013/0030358 A1 | 1/2013 | Yodfat et al. |
| 2013/0158503 A1 | 6/2013 | Kanderian, Jr. et al. |
| 2013/0178791 A1 | 7/2013 | Javitt |
| 2013/0231642 A1 | 9/2013 | Doyle et al. |
| 2013/0253472 A1 | 9/2013 | Cabiri |
| 2013/0261406 A1 | 10/2013 | Rebec et al. |
| 2013/0296823 A1 | 11/2013 | Melker et al. |
| 2013/0317753 A1 | 11/2013 | Kamen et al. |
| 2013/0338576 A1 | 12/2013 | OConnor et al. |
| 2014/0005633 A1 | 1/2014 | Finan |
| 2014/0200426 A1 | 1/2014 | Taub et al. |
| 2014/0066886 A1 | 3/2014 | Roy et al. |
| 2014/0074033 A1 | 3/2014 | Sonderegger et al. |
| 2014/0121635 A1 | 5/2014 | Hayter |
| 2014/0128839 A1 | 5/2014 | Dilanni et al. |
| 2014/0135880 A1 | 5/2014 | Baumgartner et al. |
| 2014/0146202 A1 | 5/2014 | Boss et al. |
| 2014/0180203 A1 | 6/2014 | Budiman et al. |
| 2014/0180240 A1 | 6/2014 | Finan et al. |
| 2014/0200559 A1 | 7/2014 | Doyle et al. |
| 2014/0230021 A1 | 8/2014 | Birthwhistle et al. |
| 2014/0276554 A1 | 9/2014 | Finan et al. |
| 2014/0276556 A1 | 9/2014 | Saint et al. |
| 2014/0278123 A1 | 9/2014 | Prodhom et al. |
| 2014/0309615 A1 | 10/2014 | Mazlish |
| 2014/0316379 A1 | 10/2014 | Sonderegger et al. |
| 2014/0325065 A1 | 10/2014 | Birtwhistle et al. |
| 2015/0018633 A1 | 1/2015 | Kovachev et al. |
| 2015/0025329 A1 | 1/2015 | Amarasingham et al. |
| 2015/0025495 A1 | 1/2015 | Peyser |
| 2015/0120317 A1 | 4/2015 | Mayou et al. |
| 2015/0134265 A1 | 5/2015 | Kohlbrecher et al. |
| 2015/0165119 A1 | 6/2015 | Palerm et al. |
| 2015/0173674 A1 | 6/2015 | Hayes et al. |
| 2015/0213217 A1 | 7/2015 | Amarasingham et al. |
| 2015/0217052 A1 | 8/2015 | Keenan et al. |
| 2015/0217053 A1 | 8/2015 | Booth et al. |
| 2015/0265767 A1 | 9/2015 | Vazquez et al. |
| 2015/0306314 A1 | 10/2015 | Doyle et al. |
| 2015/0351671 A1 | 12/2015 | Vanslyke et al. |
| 2015/0366945 A1 | 12/2015 | Greene |
| 2016/0015891 A1 | 1/2016 | Papiorek |
| 2016/0038673 A1 | 2/2016 | Morales |
| 2016/0038689 A1 | 2/2016 | Lee et al. |
| 2016/0051749 A1 | 2/2016 | Istoc |
| 2016/0082187 A1 | 3/2016 | Schaible et al. |
| 2016/0089494 A1 | 3/2016 | Guerrini |
| 2016/0175520 A1 | 6/2016 | Palerm et al. |
| 2016/0228641 A1 | 8/2016 | Gescheit et al. |
| 2016/0243318 A1 | 8/2016 | Despa et al. |
| 2016/0256087 A1 | 9/2016 | Doyle et al. |
| 2016/0287512 A1 | 10/2016 | Cooper et al. |
| 2016/0302054 A1 | 10/2016 | Kimura et al. |
| 2016/0331310 A1 | 11/2016 | Kovatchev |
| 2016/0354543 A1 | 12/2016 | Cinar et al. |
| 2017/0049386 A1 | 2/2017 | Abraham et al. |
| 2017/0143899 A1 | 5/2017 | Gondhalekar et al. |
| 2017/0143900 A1 | 5/2017 | Rioux et al. |
| 2017/0156682 A1 | 6/2017 | Doyle et al. |
| 2017/0173261 A1 | 6/2017 | OConnor et al. |
| 2017/0189625 A1 | 7/2017 | Cirillo et al. |
| 2017/0281877 A1 | 10/2017 | Marlin et al. |
| 2017/0296746 A1 | 10/2017 | Chen et al. |
| 2017/0311903 A1 | 11/2017 | Davis et al. |
| 2017/0348482 A1 | 12/2017 | Duke et al. |
| 2018/0036495 A1 | 2/2018 | Searle et al. |
| 2018/0040255 A1 | 2/2018 | Freeman et al. |
| 2018/0075200 A1 | 3/2018 | Davis et al. |
| 2018/0075201 A1 | 3/2018 | Davis et al. |
| 2018/0075202 A1 | 3/2018 | Davis et al. |
| 2018/0092576 A1 | 4/2018 | O'Connor et al. |
| 2018/0126073 A1 | 5/2018 | Wu et al. |
| 2018/0169334 A1 | 6/2018 | Grosman et al. |
| 2018/0200434 A1 | 7/2018 | Mazlish et al. |
| 2018/0200438 A1 | 7/2018 | Mazlish et al. |
| 2018/0200441 A1 | 7/2018 | Desborough et al. |
| 2018/0204636 A1 | 7/2018 | Edwards et al. |
| 2018/0277253 A1 | 9/2018 | Gondhalekar et al. |
| 2018/0289891 A1 | 10/2018 | Finan et al. |
| 2018/0296757 A1 | 10/2018 | Finan et al. |
| 2018/0342317 A1 | 11/2018 | Skirble et al. |
| 2018/0369479 A1 | 12/2018 | Hayter et al. |
| 2019/0076600 A1 | 3/2019 | Grosman et al. |
| 2019/0240403 A1 | 8/2019 | Palerm et al. |
| 2019/0290844 A1 | 9/2019 | Monirabbasi et al. |
| 2019/0336683 A1 | 11/2019 | O'Connor et al. |
| 2019/0336684 A1 | 11/2019 | O'Connor et al. |
| 2019/0348157 A1 | 11/2019 | Booth et al. |
| 2020/0046268 A1 | 2/2020 | Patek et al. |
| 2020/0101222 A1 | 4/2020 | Lintereur et al. |
| 2020/0101223 A1 | 4/2020 | Lintereur et al. |
| 2020/0101225 A1 | 4/2020 | O'Connor et al. |
| 2020/0219625 A1 | 7/2020 | Kahlbaugh |
| 2020/0342974 A1 | 10/2020 | Chen et al. |
| 2021/0050085 A1 | 2/2021 | Hayter et al. |
| 2021/0098105 A1 | 4/2021 | Lee et al. |
| 2022/0023536 A1 | 1/2022 | Graham et al. |

FOREIGN PATENT DOCUMENTS

| | | | |
|---|---|---|---|
| CA | 3051543 A1 * | 2/2020 | ........ A61M 5/14212 |
| CN | 1297140 A | 5/2001 | |
| DE | 19756872 A1 | 7/1999 | |
| EP | 0341049 A2 | 11/1989 | |
| EP | 0496305 A2 | 7/1992 | |
| EP | 0549341 A1 | 6/1993 | |
| EP | 1491144 A1 | 12/2004 | |
| EP | 0801578 B1 | 7/2006 | |
| EP | 2666520 A1 | 10/2009 | |
| EP | 2139382 A1 | 1/2010 | |
| EP | 2397181 A1 | 12/2011 | |
| EP | 2695573 A2 | 2/2014 | |
| EP | 2830499 A1 | 2/2015 | |

(56) References Cited

FOREIGN PATENT DOCUMENTS

| | | |
|---|---|---|
| EP | 2943149 A1 | 11/2015 |
| EP | 3177344 A1 | 6/2017 |
| EP | 3314548 A1 | 5/2018 |
| EP | 1571582 B1 | 4/2019 |
| EP | 2897071 B1 | 5/2019 |
| EP | 3607985 A1 | 2/2020 |
| GB | 2443261 A | 4/2008 |
| JP | S51125993 A | 11/1976 |
| JP | 02131777 A | 5/1990 |
| JP | 2004283378 A | 10/2007 |
| JP | 2017525451 A | 9/2017 |
| JP | 2018153569 A | 10/2018 |
| JP | 2019525276 A | 9/2019 |
| NO | 2012177353 A1 | 12/2012 |
| NO | 2015081337 A2 | 6/2015 |
| TW | 200740148 A | 10/2007 |
| TW | M452390 U | 5/2013 |
| WO | 9800193 A1 | 1/1998 |
| WO | 9956803 A1 | 11/1999 |
| WO | 0030705 A1 | 6/2000 |
| WO | 0032258 A1 | 6/2000 |
| WO | 0172354 A2 | 10/2001 |
| WO | 2002015954 A1 | 2/2002 |
| WO | 0243866 A2 | 6/2002 |
| WO | 02082990 A1 | 10/2002 |
| WO | 03016882 A1 | 2/2003 |
| WO | 03039362 A1 | 5/2003 |
| WO | 03045233 A1 | 6/2003 |
| WO | 05110601 A1 | 5/2004 |
| WO | 2004043250 A1 | 5/2004 |
| WO | 04092715 A1 | 10/2004 |
| WO | 2005051170 A2 | 6/2005 |
| WO | 2005082436 A1 | 9/2005 |
| WO | 2005113036 A1 | 12/2005 |
| WO | 2006053007 A2 | 5/2006 |
| WO | 2007064835 A2 | 6/2007 |
| WO | 2007078937 A1 | 7/2007 |
| WO | 2008024810 A2 | 2/2008 |
| WO | 2008029403 A1 | 3/2008 |
| WO | 2008133702 A1 | 11/2008 |
| WO | 2009045462 A1 | 4/2009 |
| WO | 2009049252 A1 | 4/2009 |
| WO | 2009066287 A3 | 5/2009 |
| WO | 2009066288 A1 | 5/2009 |
| WO | 2009098648 A2 | 8/2009 |
| WO | 2009134380 A2 | 11/2009 |
| WO | 2010053702 A1 | 5/2010 |
| WO | 2010132077 A1 | 11/2010 |
| WO | 2010138848 A1 | 12/2010 |
| WO | 2010147659 A2 | 12/2010 |
| WO | 2011095483 A1 | 8/2011 |
| WO | 2012045667 A2 | 4/2012 |
| WO | 2012108959 A1 | 8/2012 |
| WO | 2012134588 A1 | 10/2012 |
| WO | 2012178134 A2 | 12/2012 |
| WO | 2013078200 A1 | 5/2013 |
| WO | 2013134486 A2 | 9/2013 |
| WO | 20130149186 A1 | 10/2013 |
| WO | 2013177565 A1 | 11/2013 |
| WO | 2013182321 A1 | 12/2013 |
| WO | 2014109898 A1 | 7/2014 |
| WO | 2014110538 A1 | 7/2014 |
| WO | 2014194183 A2 | 12/2014 |
| WO | 2015056259 A1 | 4/2015 |
| WO | 2015061493 A1 | 4/2015 |
| WO | 2015073211 A1 | 5/2015 |
| WO | 2015187366 A1 | 12/2015 |
| WO | 2016004088 A1 | 1/2016 |
| WO | 2016022650 A1 | 2/2016 |
| WO | 2016041873 A1 | 3/2016 |
| WO | 2016089702 A1 | 6/2016 |
| WO | 2016141082 A1 | 9/2016 |
| WO | 2016161254 A1 | 10/2016 |
| WO | 2017004278 A1 | 1/2017 |
| WO | 2017091624 A1 | 6/2017 |
| WO | 2017105600 A1 | 6/2017 |
| WO | 2017184988 A1 | 10/2017 |
| WO | 2017205816 A1 | 11/2017 |
| WO | 2018009614 A1 | 1/2018 |
| WO | 2018067748 A1 | 4/2018 |
| WO | 2018120104 A1 | 7/2018 |
| WO | 2018136799 A1 | 7/2018 |
| WO | 2018204568 A1 | 11/2018 |
| WO | 2019077482 A1 | 4/2019 |
| WO | 2019094440 A1 | 5/2019 |
| WO | 2019213493 A1 | 11/2019 |
| WO | 2019246381 A1 | 12/2019 |
| WO | 2020081393 A1 | 4/2020 |
| WO | 2021011738 A1 | 1/2021 |

OTHER PUBLICATIONS

International Search Report and Written Opinion for International Patent Application No. PCT/US2021/051027, dated Jan. 7, 2022, 16 pages.
International Search Report and Written Opinion for International Patent Application No. PCT/US2021/052372, dated Jan. 26, 2022, 15 pages.
International Search Report and Written Opinion for the International Patent Application No. PCT/US2021/046607, dated Jan. 31, 2022, 20 pages.
International Search Report and Written Opinion for the International Patent Application No. PCT/US2021/055745, dated Feb. 14, 2022, 13 pages.
Anonymous: "Artificial pancreas—Wikipedia", Mar. 13, 2018 (Mar, 13 2018), XP055603712, Retrieved from the Internet: URL: https://en.wikipedia.org/wiki/Artificial_pancreas [retrieved on Jul. 9, 2019] section "Medical Equipment" and the figure labeled "The medical equipment approach to an artifical pancreas".
Kaveh et al., "Blood Glucose Regulation via Double Loop Higher Order Sliding Mode Control and Multiple Sampling Rate." Paper presented at the proceedings of the 17th IFAC World Congress, Seoul, Korea (Jul. 2008).
Dassau et al., "Real-Time Hypoglycemia Prediction Suite Using Contineous Glucose Monitoring," Diabetes Care, vol. 33, No. 6, 1249-1254 (2010).
International Search Report and Written Opinion for International Patent Application No. PCT/US17/53262, dated Dec. 13, 2017, 8 pages.
Van Heusden et al., "Control-Relevant Models for Glucose Control using A Priori Patient Characteristics", IEEE Transactions on Biomedical Engineering, vol. 59, No. 7, (Jul. 1, 2012) pp. 1839-1849.
Doyle III et al., "Run-to-Run Control Strategy for Diabetes Management." Paper presented at 23rd Annual International Conference of the IEEE Engineering in Medicine and Biology Society, Istanbul, Turkey. (Oct. 2001).
Bequette, B.W., and Desemone, J., "Intelligent Dosing Systems": Need for Design and Analysis Based on Control Theory, Diabetes Technology and Therapeutics 9(6): 868-873 (2004).
Parker et al., "A Model-Based Agorithm for Blood Gucose Control in Type 1 Diabetic Patients." IEEE Transactions on Biomedical Engineering, 46 (2) 148-147 (1999).
International Search Report and Written Opinion for International Patent Application No. PCT/US2017/015601, dated May 16, 2017, 12 pages.
International Search Report and Written Opinion for the International Patent Application No. PCT/US2018/018901, dated Aug. 6, 2018, 12 pages.
International Search Report and Written Opinion for International Patent Application No. PCT/US2018/052467, dated Jan. 4, 2019, 13 pages.
"How to Create a QR Code that Deep Links to Your Mobile App", Pure Oxygen Labs, web<https://pureoxygenlabs.com/how-to-create-a-qr-codes-that-deep-link-to-your-mobile-app/> Year:2017.
"Read NFC Tags with an iPHone App on IOS 11", GoToTags, Sep. 11, 2017, web <https://gototags.com/blog/read-hfc-tags-with-an-iphone-app-on-ios-11/>. (Year:2017).

(56) References Cited

OTHER PUBLICATIONS

International Search Report and Written Opinion for International Patent Application No. PCT/US2016/063350, dated Mar. 27, 2017, 9 pages.
Extended Search Report dated Aug. 13, 2018, issued in European Patent Application No. 16753053.4, 9 pages.
International Search Report and Written Opinion for International Patent Application No. PCT/US16/18452, dated Apr. 29, 2015, 9 pages.
International Preliminary Report on Patentability dated Aug. 31, 2017, issued in PCT Patent Application No. PCT/US2016/018452, 7 pages.
International Search Report and Written Opinion for International Patent Application No. PCT/US2019/055862, dated Mar. 11, 2020.
International Search Report and Written Opinion for Application No. PCT/US2019/030652, dated Sep. 25, 2019, 19 pages.
International Search Report and Written Opinion for the International Patent Application No. PCT/US2022/013470, dated May 6, 2022, 14 pages.
International Search Report and Written Opinion for the International Patent Application No. PCT/US2022/013473, dated May 6, 2022, 13 pages.
International Search Report and Written Opinion for the International Patent Application No. PCT/US2022/019079, dated Jun. 2, 2022, 14 pages.
International Search Report and Written Opinion for the International Patent Application No. PCT/US2022/018453, dated Jun. 2, 2022, 13 pages.
International Search Report and Written Opinion for the International Patent Application No. PCT/US22/018700, dated Jun. 7, 2022, 13 pages.
International Search Report and Written Opinion for the International Patent Application No. PCT/US22/019080, dated Jun. 7, 2022, 14 pages.
International Search Report and Written Opinion for the International Patent Application No. PCT/US22/019664, dated Jun. 7, 2022, 14 pages.
International Search Report and Written Opinion for the International Patent Application No. PCT/US21/060618, dated Mar. 21, 2022, 15 pages.
Herrero Pau et al.: "Enhancing automatic closed-loop glucose control in type 1 diabetes with an adaptive meal bolus calculator -in silicoevaluation under intra-day variability", Computer Methods and Programs in Biomedicine, Elsevier, Amsterdam, NL, vol. 146, Jun. 1, 2017 (Jun. 1, 2017), pp. 125-131, XP085115607, ISSN: 0169-2607, DOI:10.1016/J.CMPB.2017.05.010.
Marie Aude Qemerais: "Preliminary Evaluation of a New Semi-Closed-Loop Insulin Therapy System over the prandial beriod in Adult Patients with type I diabetes: the WP6. 0 Diabeloop Study", Journal of Diabetes Science and Technology Diabetes Technology Society Reprints and permissions, Jan. 1, 2014, pp. 1177-1184, Retrieved from the Internet: URL:http://journals.sagepub.com/doi/pdf/10.1177/1932296814545668 [retrieved on Jun. 6, 2022] chapter "Functioning of the Algorithm" chapter "Statistical Analysis" p. 1183, left-hand column, line 16-line 23.
Anonymous: "Kernel density estimation", Wikipedia, Nov. 13, 2020 (Nov. 13, 2020), pp. 1-12, XP055895569, Retrieved from the Internet: URL:https://en.wikipedia.org/w/index.php?title=Kernel_density_estimation&oldid=988508333 [retrieved on Jun. 6, 2022].
Anonymous: "openaps / oref0 /lib/determine-basal-js", openaps repository, Nov. 9, 2019 (Nov. 9, 2019), pp. 1-17, XP055900283, Retrieved from the Internet: URL:https://github.com/openaps/oref0/blob/master/lib/determine-basal/determine-basal.js [retrieved on Jun. 6, 2022] line 116-line 118, line 439-line 446.
Anonymous: "AndroidAPS screens", AndroidAPS documentation, Oct. 4, 2020 (Oct. 4, 2020), pp. 1-12, XP055894824, Retrieved from the Internet: URL:https://github.com/openaps/AndroidAPSdocs/blob/25d8acf8b28262b411b34f416f173ac0814d7e14/docs/EN/Getting-Started/Screenshots.md [retrieved on Jun. 6, 2022].

Kozak Milos et al.: "Issue #2473 of AndroidAPS", MilosKozak / AndroidAPS Public repository, Mar. 4, 2020 (Mar. 4, 2020), pp. 1-4, XP055900328, Retrieved from the Internet: URL:https://github.com/MilosKozak/AndroidAPS/issues/2473 [retrieved on Jun. 6, 2022].
Medication Bar Code System Implementation Planning Section I: A Bar Code Primer for Leaders, Aug. 2013.
Medication Bar Code System Implementation Planning Section II: Building the Case for Automated Identification of Medications, Aug. 2013.
Villareal et al. (2009) in: Distr. Comp. Art. Intell. Bioninf. Soft Comp. Amb. Ass. Living; Int. Work Conf. Art. Neural Networks (IWANN) 2009, Lect. Notes Comp. Sci. vol. 5518; S. Omatu et al. (Eds.), pp. 870-877.
Fox, Ian G.; Machine Learning for Physiological Time Series: Representing and Controlling Blood Glucose for Diabetes Management; University of Michigan. ProQuest Dissertations Publishing, 2020. 28240142. (Year: 2020).
International Search Report and Written Opinion for the International Patent Application No. PCT/US2022/012896, dated Apr. 22, 2022, 15 pages.
Unger, Jeff, et al., "Glucose Control in the Hospitalized Patient," Emerg. Med 36(9):12-18 (2004).
"Glucommander FAQ" downloaded from https://adaendo.com/GlucommanderFAQ.html on Mar. 16, 2009.
Finfer, Simon & Heritier, Stephane. (2009). The NICE-SUGAR (Normoglycaemia in Intensive Care Evaluation and Survival Using Glucose Algorithm Regulation) Study: statistical analysis plan. Critical care and resuscitation : journal of the Australasian Academy of Critical Care Medicine. 11. 46-57.
Letters to the Editor regarding "Glucose Control in Critically Ill Patients," N Engl J Med 361: 1, Jul. 2, 2009.
"Medtronic is Leading a Highly Attractive Growth Market," Jun. 2, 2009.
Davidson, Paul C., et al. "Glucommander: An Adaptive, Computer-Directed System for IV Insulin Shown to be Safe, Simple, and Effective in 120,618 Hours of Operation," Atlanta Diabetes Associates presentation.
Davidson, Paul C., et al. "Pumpmaster and Glucommander," presented at the MiniMed Symposium, Atlanta GA, Dec. 13, 2003.
Kanji S., et al. "Reliability of point-of-care testing for glucose measurement in critically ill adults," Critical Care Med, vol. 33, No. 12, pp. 2778-2785, 2005.
Krinsley James S., "Severe hypoglycemia in critically ill patients: Risk factors and outcomes," Critical Care Med, vol. 35, No. 10, pp. 1-6, 2007.
International Search Report and Written Opinion for the International Patent Application No. PCT/US2021/016283, dated Jun. 2, 2021, 15 pages.
Farkas et al. "Single-Versus Triple-Lumen Central Catheter-Related Sepsis: A Prospective Randomized Study in a Critically Ill Population" The American Journal of Medicine Sep. 1992 vol. 93 p. 277-282.
Davidson, Paul C., et al., A computer-directed intravenous insulin system shown to be safe, simple, and effective in 120,618 h of operation, Diabetes Care, vol. 28, No. 10, Oct. 2005, pp. 2418-2423.
R Anthony Shaw, et al., "Infrared Spectroscopy in Clinical and Dianostic Analysis," Encyclopedia of Analytical Chemistry, ed. Robert A. Meyers, John Wiley & Sons, Ltd., pp. 1-20, 2006.
Gorke, A "Microbial Contamination of Haemodialysis Catheter Connections" Journal of Renal Care,European Dialysis & Transplant Nurses Association.
Lovich et al. "Central venous catheter infusions: A laboratory model shows large differences in drug delivery dynamics related to catheter dead volume" Critical Care Med 2007 vol. 35, No. 12.
Van Den Berghe, Greet, M.D., Ph.D., et al., Intensive Insulin Therapy in Critically Ill Patients, The New England Journal of Medicine, vol. 345, No. 19, Nov. 8, 2001, pp. 1359-1367.
Templeton et al., "Multilumen Central Venous Catheters Increase Risk for Catheter-Related Bloodstream Infection: Prospective Surveillance Study".
Wilson, George S., et al., Progress toward the Development of an Implantable Sensor for Glucose, Clin. Chem., vol. 38, No. 9, 1992, pp. 1613-1617.

(56) References Cited

OTHER PUBLICATIONS

Yeung et al. "Infection Rate for Single Lumen v Triple Lumen Subclavian Catheters" Infection Control and Hospital Epidemiology, vol. 9, No. 4 (Apr. 1988) pp. 154-158 The University of Chicago Press.

International Search Report and Written Opinion, International Application No. PCT/US2010/033794 dated Jul. 16, 2010.

International Search Report and Written Opinion in PCT/US2008/079641 dated Feb. 25, 2009.

Berger, "Measurement of Analytes in Human Serum and Whole Blood Samples by Near-Infrared Raman Spectroscopy," Ph.D. Thesis, Massachusetts Institute of Technology, Chapter 4, pp. 50-73, 1998.

Berger, "An Enhanced Algorithm for Linear Multivariate Calibration," Analytical Chemistry, vol. 70, No. 3, pp. 623-627, Feb. 1, 1998.

Billman et al., "Clinical Performance of an in line Ex-Vivo Point of Care Monitor: A Multicenter Study," Clinical Chemistry 48: 11, pp. 2030-2043, 2002.

Widness et al., "Clinical Performance on an In-Line Point-of-Care Monitor in Neonates"; Pediatrics, vol. 106, No. 3, pp. 497-504, Sep. 2000.

Finkielman et al., "Agreement Between Bedside Blood and Plasma Glucose Measurement in the ICU Setting"; retrieved from http://www.chestjournal.org; CHEST/127/5/May 2005.

Glucon Critical Care Blood Glucose Monitor; Glucon; retrieved from http://www.glucon.com.

Fogt, et al., "Development and Evaluation of a Glucose Analyzer for a Glucose-Controlled Insulin Infusion System (Biostator)"; Clinical Chemistry, vol. 24, No. 8, pp. 1366-1372, 1978.

Vonach et al., "Application of Mid-Infrared Transmission Spectrometry to the Direct Determination of Glucose in Whole Blood," Applied Spectroscopy, vol. 52, No. 6, 1998, pp. 820-822.

Muniyappa et al., "Current Approaches for assessing insulin sensitivity and resistance in vivo: advantages, imitations, and appropriate usage," AJP-Endocrinol Metab, vol. 294, E15-E26, first published Oct. 23, 2007.

International Preliminary Report on Patentability for the International Patent Application No. PCT/US2019/053603, dated Apr. 8, 2021, 9 pages.

International Search Report and Written Opinion for the International Patent Application No. PCT/US2019/053603, dated Jan. 7, 2020, 16 pages.

Dassau et al., "Detection of a meal using continuous glucose monitoring: Implications for an artificial [beta]-cell." Diabetes Care, American Diabetes Association, Alexandria, VA, US, 31(2):295-300 (2008).

Cameron et al., "Probabilistic Evolving Meal Detection and Estimation of Meal Total Glucose Appearance Author Affiliations", J Diabetes Sci and Tech, vol. Diabetes Technology Society ;(5): 1022-1030 (2009).

Lee et al., "A closed-loop artificial pancreas based on model predictive control: Human-friendly identification and automatic meal disturbance rejection", Biomedical Signal Processing and Control, Elsevier, Amsterdam, NL, 4 (4):1746-8094 (2009).

Anonymous: "Fuzzy control system", Wikipedia, Jan. 10, 2020. URL: https://en.wikipedia.org/w/index.php?title=Fuzzy_control_system&oldid=935091190.

An Emilia Fushimi: "Artificial Pancreas: Evaluating the ARG Algorithm Without Meal Annoucement", Journal of Diabetes Science and Technology Diabetes Technology Society, Mar. 22, 2019, pp. 1025-1043.

International Search Report and Written Opinion for the InternationalPatent Application No. PCT/US2021/017441, dated May 25, 2021, 12 pages.

Mirko Messori et al.: "Individualized model predictive control for the artificial pancreas: In silico evaluation of closed-loop glucose control", IEEE Control Systems, vol. 38, No. 1, Feb. 1, 2018, pp. 86-104.

International Search Report and Written Opinion for the International Patent Application No. PCT/US2021/017662, dated May 26, 2021, 14 pages.

Anonymous: "Reservoir Best Practice and Top Tips" Feb. 7, 2016, URL: https://www.medtronic-diabetes.co.uk/blog/reservoir-best-practice-and-top-tips, p. 1.

Gildon Bradford: "InPen Smart Insulin Pen System: Product Review and User Experience" Diabetes Spectrum, vol. 31, No. 4, Nov. 15, 2018, pp. 354-358.

International Search Report and Written Opinion for the International Patent Application No. PCT/US2021/016050, dated May 27, 2021, 16 pages.

International Search Report and Written Opinion for the International Patent Application No. PCT/US2020/065226, dated May 31, 2021, 18 pages.

International Search Report and Written Opinion for the International Patent Application No. PCT/US2021/017659, dated May 31, 2021, 13 pages.

Montaser Eslam et al., "Seasonal Local Models for Glucose Prediction in Type 1 Diabetes", IEE Journal of Biomedical and Health Informatics, IEEE, Piscataway, NJ, USA, vol. 24, No. 7, Nov. 29, 2019, pp. 2064-2072.

Samadi Sediqeh et al., "Automatic Detection and Estimation of Unannouced Meals for Multivariable Artificial Pancreas System", Diabetis Technology & Therapeutics, vol. 20m No. 3, Mar. 1, 2018, pp. 235-246.

Samadi Sediqeh et al., "Meal Detection and Carbohydrate Estimation Using Continuous Glucose Sensor Data" IEEE Journal of Biomedical and Health Informatics, IEEE, Piscataway, NJ, USA, vol. 21, No. 3, May 1, 2017, pp. 619-627.

Khodaei et al., "Physiological Closed-Loop Contol (PCLC) Systems: Review of a Modern Frontier in Automation", IEEE Access, IEEE, USA, vol. 8, Jan. 20, 2020, pp. 23965-24005.

E. Atlas et al., "MD-Logic Artificial Pancreas System: A pilot study in adults with type 1 diabetes", Diabetes Care, vol. 33, No. 5, Feb. 11, 2010, pp. 1071-1076.

International Search Report and Written Opinion for the International Patent Application No. PCT/US2020/052125, dated Aug. 12, 2020, 15 pages.

International Search Report and Written Opinion for the International Patent Application No. PCT/US2020/050332, dated Sep. 12, 2020, 12 pages.

European Patent Office, "Notification of Transmittal of the ISR and the Written Opinion of the International Searching Authority, or the Declaration," in PCT Application No. PCT/GB2015/050248, dated Jun. 23, 2015, 12 pages.

International Search Report and Written Opinion for the International Patent Application No. PCT/US2021/012246, dated Apr. 13, 2021, 15 pages.

International Search Report and Written Opinion for the International Patent Application No. PCT/US2021/013639, dated Apr. 28, 2021, 14 pages.

International Search Report and Written Opinion for the International Patent Application No. PCT/US2020/063326, dated May 3, 2021, 17 pages.

International Search Report and Written Opinion for the International Patent Application No. PCT/US2021/022694, dated Jun. 25, 2021, 13 pages.

International Search Report and Written Opinion for the International Patent Application No. PCT/US2021/017664, dated May 26, 2021, 16 pages.

European Search Report for the European Patent Application No. 21168591.2, dated Oct. 13, 2021, 04 pages.

International Search Report and Written Opinion for the International Patent Application No. PCT/US2021/041954, dated Oct. 25, 2021, 13 pages.

International Search Report and Written Opinion for the International Patent Application No. PCT/US2021/047771, dated Dec. 22, 2021, 11 pages.

International Search Report and Written Opinion for the International Patent Application No. PCT/US2021/052855, dated Dec. 22, 2021, 11 pages.

(56) References Cited

OTHER PUBLICATIONS

International Preliminary Report on Patentability, PCT Application No. PCT/US2022/019080, dated Sep. 12, 2023, 9 pages.

* cited by examiner

800

Mixed Scaling for Insulin

802 — Set a Substantially Zero Cost Below a First Threshold

804 — Set a Quadratic Penalty Near Target Blood Glucose Concentration or Near Basal Insulin Dosage 806 — Set a Linear Penalty When Blood Glucose Concentration or Insulin Dosage is Above a Second Threshold Done

FIG. 8A

ADAPTABLE ASYMMETRIC MEDICAMENT COST COMPONENT IN A CONTROL SYSTEM FOR MEDICAMENT DELIVERY

CROSS-REFERENCE TO RELATED APPLICATIONS

This application claims the benefit to U.S. Provisional Application No. 63/165,252, filed Mar. 24, 2021, and U.S. Provisional Application No. 63/158,918, filed Mar. 10, 2021, the entire contents of which are incorporated herein by reference in their entirety.

BACKGROUND

Some control systems seek to minimize a cost function. An example of such a control system is a control device for a medicament delivery device, such as an automatic insulin delivery (AID) device. The cost function for an AID device typically weighs the risk of under-delivery or over-delivery of insulin versus the risk of glucose excursions under or over a control target. In some AID devices, the cost function sums a glucose cost component and an insulin cost component. The glucose component captures the magnitude of glucose excursions above and/or below the control target that are predicted with a candidate dosage, and the insulin component captures the magnitude of insulin above or below a standard dosage (such as a basal dosage) that would be delivered with the candidate dosage. The control system applies the cost function to each candidate dosage of insulin and chooses the candidate dosage with the minimum cost.

AID systems assume that the basal dosage will maintain the blood glucose concentration at a target blood glucose concentration. Unfortunately, this assumption does not hold true for many users. The formulation for the standard basal dosage (e.g., basal dosage calculated from total daily insulin (TDI)) does not match the true needs of many users. For example, suppose that a user needs more than a standard basal dosage of insulin. Candidate dosages above the standard basal dosage are punished by the insulin cost component of the cost function. The insulin cost component is a quadratic expression in the formulation of the cost function. Hence, the magnitude of the insulin cost component escalates rapidly as the candidate dosages increase above the standard basal dosage. This makes it difficult to compensate for lower magnitude glucose excursions because the cost for suitable candidate dosages to rectify the lower magnitude glucose gets high rapidly due to the rapidly escalating insulin cost component. The system thus prefers smaller changes to insulin dosages rather than larger changes, so it may take a long period of time to compensate for such lower magnitude glucose excursions. As such, the user may have persistent low magnitude glucose excursions, which may not be healthy for the patient. The result is that the user may have a persistently higher or lower than target blood glucose concentration.

Another difficulty with the standard formulation of the cost function for AID systems is that there is a penalty for decreasing insulin delivery since there is a delta relative to the basal dosage. This is problematic in instances where the dosage should be quickly decreased to avoid the risk of the user going into hypoglycemia.

SUMMARY

In accordance with a first inventive aspect, a medicament delivery device includes a memory for storing data and computer programming instructions and a pump for delivering a medicament to a user. The medicament delivery device further includes a processor for executing the computer programming instructions to determine values of a cost function for candidate dosages to the user. The cost function has a performance cost component (e.g., for glucose excursions from a desired target) and a medicament cost component. The medicament cost component is configured to be asymmetrical about a threshold, standard basal, or a customized amount configured to the user. The processor also is configured for executing the computer programming instructions to choose a dosage to be delivered to the user by the pump from among the candidate dosages based on values of the cost function for the candidate dosages.

The threshold amount may be an average basal dosage or a particular basal dosage for the user. The threshold amount may be a multiple of a basal dosage amount for the user, and the multiple is greater than one. The multiple may be a ratio of mean blood glucose concentration over a time interval to target blood glucose concentration. The multiple may be a ratio of average basal dosage delivered to the user over an interval to an estimate of basal dosage over the interval derived from total daily medicament for the user. The choosing of the dosage may comprise choosing one of the candidate dosages with the lowest value for the cost function. The medicament delivery device may deliver at least one of insulin, a glucagon-like peptide (GLP-1) agonist, pramlintide, co-formulations thereof, or another type of drug. The medicament cost component may be zero or substantially zero for any of the candidate dosages below the threshold amount.

In accordance with another inventive aspect, a medicament delivery device includes a memory for storing data and computer programming instructions and a pump for delivering a medicament to a user. The medicament delivery device includes a processor for executing the computer programming instructions to determine values of a cost function for candidate dosages of the medicament for the user and to choose as a dosage to be delivered to the user by the pump among the candidate dosages based on values of the cost function for the candidate dosages. The cost function has a performance cost component and a medicament cost component. The scaling of the medicament cost component is quadratic above a first threshold and linear above a second threshold that is greater than the first threshold.

The scaling of the medicament cost component may be linear below the first threshold. The medicament cost component may have a fixed value for at least one of the candidate dosages that is below the first threshold. The fixed value may be zero or substantially zero.

In accordance with a further inventive aspect, a medicament delivery device includes a memory for storing data and computer programming instructions and a pump for delivering a medicament to a user. The medicament delivery device also includes a processor for executing the computer programming instructions to determine values of a cost for candidate dosages to the user and to choose as a dosage to be delivered to the user by the pump among the candidate dosages to the user based on the values of the cost for the candidate dosages. The cost has a performance cost component and a medicament cost component. The cost is calculated in a different manner for different ranges of the candidate dosages.

The cost may be calculated to be negligible for any one of the candidate dosages in one of the ranges below a first threshold. The first threshold may be an average basal dosage or a particular basal dosage for the user. The first threshold may be a multiple of the average basal dosage or the particular basal dosage for the user, and the multiple may be greater than one. The cost may include a medicament cost component that is calculated by a quadratic formulation in a one of the ranges above a second threshold that is greater than the first threshold. The cost may include a medicament cost component that is calculated by a linear formulation in a one of the ranges above a third threshold that is greater than the second threshold. The cost may be calculated using a cost function, and the cost function may scale differently in at least two of the ranges. The cost function may include a performance cost component and a medicament cost component, and the medicament cost component may differ in the at least two of the ranges to cause the cost function to scale differently in the at least two of the ranges. The cost function may have a medicament cost component, and the cost may be determined for a first of the ranges using a different formula for medicament cost than used in determining the cost for a second of the ranges. The cost may be determined by a different cost function for each range. The medicament may be one of insulin, a glucagon-like peptide-1 (GLP-1) agonist, pramlintide, co-formulations thereof, or another type of drug.

BRIEF DESCRIPTION OF THE DRAWINGS

FIG. 8A depicts a flowchart of illustrative steps that may be performed to provide mixed scaling across ranges of candidate medicament dosages in exemplary embodiments.

DETAILED DESCRIPTION

Figure 1:
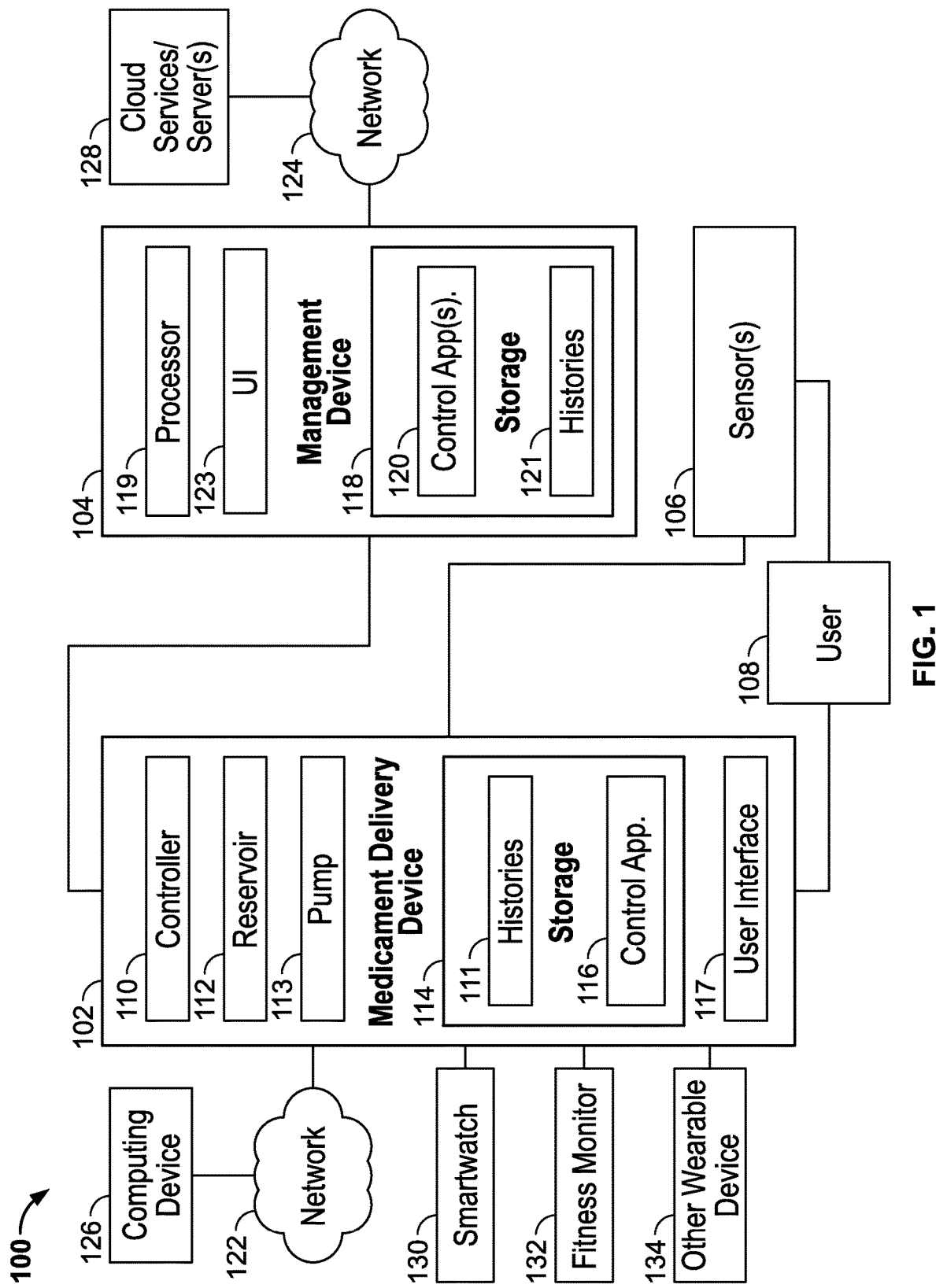
FIG. 1 depicts an illustrative medicament delivery system that is suitable for delivering a medicament in accordance with exemplary embodiments.

The exemplary embodiments concern medicament delivery devices that use cost functions in their control systems to determine medicament dosages. The cost function may have a medicament cost component and a performance cost component. The exemplary embodiments may use cost functions having medicament cost components that scale asymmetrically for different ranges of inputs (i.e., different candidate medicament dosages). The variance in scaling for different input ranges provides added flexibility to tailor the medicament cost component to the user and thus provide better management of medicament delivery to the user and better conformance to a performance target.

The medicament delivery devices of the exemplary embodiments may deliver any of a wide variety of medicaments. The medicaments delivered by the medicament delivery devices of the exemplary embodiments may include but are not limited to insulin, glucagon-like peptide-1 (GLP-1) agonists, pramlintide, co-formulations of two or more of the foregoing, glucagon, hormonal agents, pain management agents, chemotherapy agents, antibiotic agents, anti-viral agents, blood thinning agents, blood clotting agents, anti-depressive agents, anti-seizure agents, anti-psychotic agents, blood pressure reducing agents, statins, therapeutic agents and pharmaceutical agents.

The exemplary embodiments may provide modifications to the cost function of a medicament delivery device relative to conventional medicament delivery devices. For example, the exemplary embodiments may use a cost function that has a medicament cost component (such as an insulin cost component) of zero for candidate dosages for a range of candidate dosages (e.g., below a reference dosage). Alternatively, the medicament cost component may have a negligible value, such as one that is substantially zero, for a range of candidate dosages. For an insulin or GLP-1 agonists delivery device, this reduces the medicament cost component so that there is a reduced penalty for decreasing medicament dosage and makes it easier to avoid hypoglycemia in some instances. This modification to the medicament cost component is configured to reflect the view that the consequences of hypoglycemia are generally more dangerous than hyperglycemia.

In other exemplary embodiments, the medicament cost component may have a fixed positive value (i.e., is a constant value) for candidate dosages in a range. In still other exemplary embodiments, the medicament cost component may be a linear expression in the formulation of the cost function for candidate dosages in a range of candidate dosages. The net effect of these changes to the conventional medicament cost component is to decrease the penalty resulting from the medicament cost component for candidate dosages below the standard dosage relative to the conventional medicament cost component.

The cost function need not use a singular expression or a single type of expression for the medicament cost component over the range of all possible candidate dosages. The medicament cost expression may be a constant, a linear expression, a quadratic expression or an exponential expression that is not quadratic. The medicament cost component may have different expressions over ranges of candidate dosages. For example, a medicament cost component may be a constant for a first range of candidate dosages, a non-constant linear expression for a second range of candidate dosages and a quadratic expression for a third range of candidate dosages. In some embodiments, the medicament cost component expression may be of a single type (e.g., constant, linear, quadratic or exponential) over the range of candidate dosages but may have a different formulation. For example, the medicament cost component may be expressed as $x+2$ for a first range and $2x+3$ for a different range, where x is a variable such as a delta relative to a basal dosage.

In some exemplary embodiments, different formulations of the cost function may be used for different ranges or even different cost functions may be used for different ranges. The differences need not be due solely to changes to the medicament cost component. The scaling of the medicament cost component need not be the same over all possible candidate dosages. The cost function may be asymmetric across a threshold or reference dosage.

The exemplary embodiments may also change the reference dosage that is used in determining the medicament cost component. First, the reference dosage may be set higher than a basal dosage. Thus, the reference dosage may be better suited for a user with higher than normal medicament needs, such as higher insulin needs. Second, the reference dosage may be customized to a user's actual average basal amount (such as an average over a recent interval). This tailors the reference dosage value better to the user. Third, the reference dosage may be customized based on a user's recent actual split between basal delivery of medicament and bolus delivery of medicament. The reference dosage is not limited to being 50% of TDI in the cost calculation.

FIG. 1 depicts an illustrative medicament delivery system 100 that is suitable for delivering a medicament, such as insulin, a GLP-1 agonist or other medicament like those detailed above, to a user 108 in accordance with exemplary embodiments. The medicament delivery system 100 includes a medicament delivery device 102. The medicament delivery device 102 may be a wearable device that is worn on the body of the user 108. The medicament delivery device 102 may be directly coupled to a user (e.g., directly attached to a body part and/or skin of the user 108 via an adhesive or the like). In an example, a surface of the medicament delivery device 102 may include an adhesive to facilitate attachment to the user 108.

The medicament delivery device 102 may include a controller 110. The controller 110 may be implemented in hardware, software, or any combination thereof. The controller 110 may, for example, be a microprocessor, a logic circuit, a field programmable gate array (FPGA), an application specific integrated circuit (ASIC) or a microcontroller coupled to a memory. The controller 110 may maintain a date and time as well as other functions (e.g., calculations or the like). The controller 110 may be operable to execute a control application 116 stored in the storage 114 that enables the controller 110 to implement a control system for controlling operation of the medicament delivery device 102. The control application 116 may control medicament delivery to the user 108 as described herein. The storage 114 may hold histories 111 for a user, such as a history of automated medicament deliveries, a history of bolus medicament deliveries, meal event history, exercise event history, sensor data and the like. In addition, the controller 110 may be operable to receive data or information. The storage 114 may include both primary memory and secondary memory. The storage 114 may include random access memory (RAM), read only memory (ROM), optical storage, magnetic storage, removable storage media, solid state storage or the like.

The medicament delivery device 102 may include a reservoir 112 for storing medicament for delivery to the user 108 as warranted. A fluid path to the user 108 may be provided, and the medicament delivery device 102 may expel the medicament from the reservoir 112 to deliver the medicament to the user 108 via the fluid path. The fluid path may, for example, include tubing coupling the medicament delivery device 102 to the user 108 (e.g., tubing coupling a cannula to the reservoir 112).

There may be one or more communications links with one or more devices physically separated from the medicament delivery device 102 including, for example, a management device 104 of the user and/or a caregiver of the user and/or a sensor 106. The communication links may include any wired or wireless communication link operating according to any known communications protocol or standard, such as Bluetooth®, Wi-Fi, a near-field communication standard, a cellular standard, or any other wireless protocol The medicament delivery device 102 may also include a user interface 117, such as an integrated display device for displaying information to the user 108 and in some embodiments, receiving information from the user 108. The user interface 117 may include a touchscreen and/or one or more input devices, such as buttons, a knob or a keyboard.

The medicament delivery device 102 may interface with a network 122. The network 122 may include a local area network (LAN), a wide area network (WAN) or a combination therein. A computing device 126 may be interfaced with the network, and the computing device may communicate with the insulin delivery device 102.

The medicament delivery system 100 may include sensor (s) 106 for sensing the levels of one or more analytes. The sensor(s) 106 may be coupled to the user 108 by, for example, adhesive or the like and may provide information or data on one or more medical conditions and/or physical attributes of the user 108. The sensor(s) 106 may, in some exemplary embodiments, provide periodic blood glucose concentration measurements and may be a continuous glucose monitor (CGM), or another type of device or sensor that provides blood glucose measurements. The sensor(s) 106 may be physically separate from the medicament delivery device 102 or may be an integrated component thereof. The sensor(s) 106 may provide the controller 110 with data indicative of one or more measured or detected analyte levels of the user 108. The information or data provided by the sensor(s) 106 may be used to adjust medicament delivery operations of the medicament delivery device 102.

The medicament delivery system 100 may also include the management device 104. In some embodiments, no management device 104 is needed; rather the medicament delivery device 102 may manage itself. The management device 104 may be a special purpose device, such as a dedicated personal diabetes manager (PDM) device. The management device 104 may be a programmed general-purpose device, such as any portable electronic device including, for example, a dedicated controller, such as a processor, a micro-controller or the like. The management device 104 may be used to program or adjust operation of the medicament delivery device 102 and/or the sensor 104. The management device 104 may be any portable electronic device including, for example, a dedicated device, a smartphone, a smartwatch or a tablet. In the depicted example, the management device 104 may include a processor 119 and a storage 118. The processor 119 may execute processes to manage and control the delivery of the medicament to the user 108. The processor 119 may also be operable to execute programming code stored in the storage 118. For example, the storage may be operable to store one or more control applications 120 for execution by the processor 119. The one or more control applications 120 (or 116) may be responsible for controlling the medicament delivery device 102, e.g., delivery of insulin to the user 108. The storage 118 may store the one or more control applications 120, histories 121 like those described above for the medicament delivery device 102 and other data and/or programs.

The management device 104 may include a user interface (UI) 123 for communicating with the user 108. The user interface 123 may include a display, such as a touchscreen, for displaying information. The touchscreen may also be used to receive input when it is a touch screen. The user interface 123 may also include input elements, such as a keyboard, buttons, knob(s), or the like. The user interface 123 may be used to view data or history or provide input, such as to cause a change in basal medicament dosage, deliver a bolus of medicament, or change one or more parameters used by the control app 116/120.

The management device 104 may interface with a network 124, such as a LAN or WAN or combination of such networks. The management device 104 may communicate over network 124 with one or more servers or cloud services 128.

Other devices, like smartwatch 130, fitness monitor 132 and/or another wearable device 134 may be part of the medicament delivery system 100. These devices may communicate with the medicament delivery device 102 to receive information and/or issue commands to the medicament delivery device 102. These devices 130, 132 and 134 may execute computer programming instructions to perform some of the control functions otherwise performed by controller 110 or processor 119. These devices 130, 132 and 134 may include displays for displaying information, e.g., analyte levels like current blood glucose level, medicament on board, medicament delivery history, etc. The display may show a user interface for providing input, such as to cause a change in basal medicament dosage, delivery of a bolus of medicament, or a change of one or more parameters used by the control application 116/120. These devices 130, 132 and 134 may also have wireless communication connections with the sensor 106 to directly receive analyte data.

Figure 2:
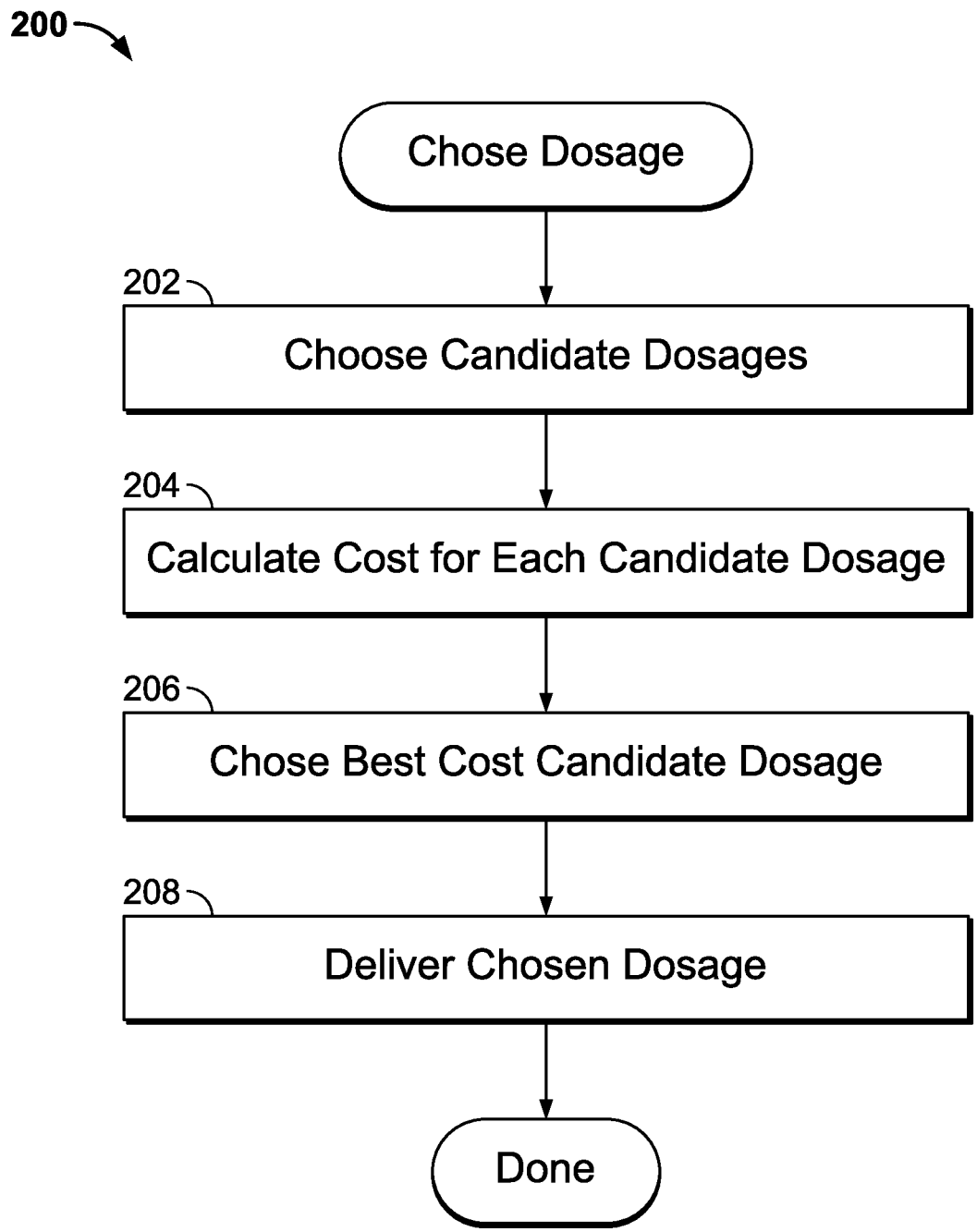
FIG. 2 depicts a flowchart of illustrative steps that may be performed in choosing a next dosage to be delivered to the user in exemplary embodiments.

The control system of the exemplary embodiments relies upon a cost function as mentioned above. The control system attempts to minimize the aggregate penalty of the cost function over a wide range of possible candidate medicament dosages. FIG. 2 depicts a flowchart 200 of illustrative steps that may be performed in choosing a next dosage to be delivered to the user in exemplary embodiments. At 202, the control system chooses the candidate dosages from which the dosage may be chosen. At 204, a cost is calculated for each candidate dosage using the cost function. The cost function has the candidate dosage as an input and the cost for the candidate dosage as an output. At 206, the candidate dosage with the best cost is chosen. Depending on how the cost function is configured, the best cost may be the lowest value or the highest value. For discussion purposes hereinafter, it is assumed that the lowest cost candidate dosage is the best cost. At 208, the chosen dosage is delivered to the user. A control signal may be generated and sent from the controller 110 running the control application 116 to the pump 113 to cause the pump 113 to deliver the chosen medicament dosage to the user. Thereafter, process 200 may be repeated for another subsequent cycle (e.g., every 5 minutes).

In order to appreciate how the exemplary embodiments modify a cost function for a medicament delivery device, it is helpful to look at a conventional cost function for a medicament device. An example of a cost function for a medicament delivery device is a cost function for an insulin delivery device. A conventional cost function for an insulin delivery device is:

$$J = Q \cdot \Sigma_{i=1}^{M} G_p(i)^2 + R \cdot \Sigma_{i=1}^{n} I_p(i)^2 \quad \text{(Equation 1)}$$

where J is the cost, Q and R are weight coefficients, $G_p(i)^2$ is the square of the deviation between a projected blood glucose concentration for a particular (e.g., candidate) insulin dosage at cycle i and the projected blood glucose concentration for the standard basal insulin dosage, M is the number of cycles in the prediction horizon (a cycle is a fixed interval, such 5 minutes), $I_p(i)^2$ is the square of the deviation between the projected insulin delivered at cycle i and the standard insulin for basal insulin delivery, and n is the control horizon in cycles.

Figure 3:
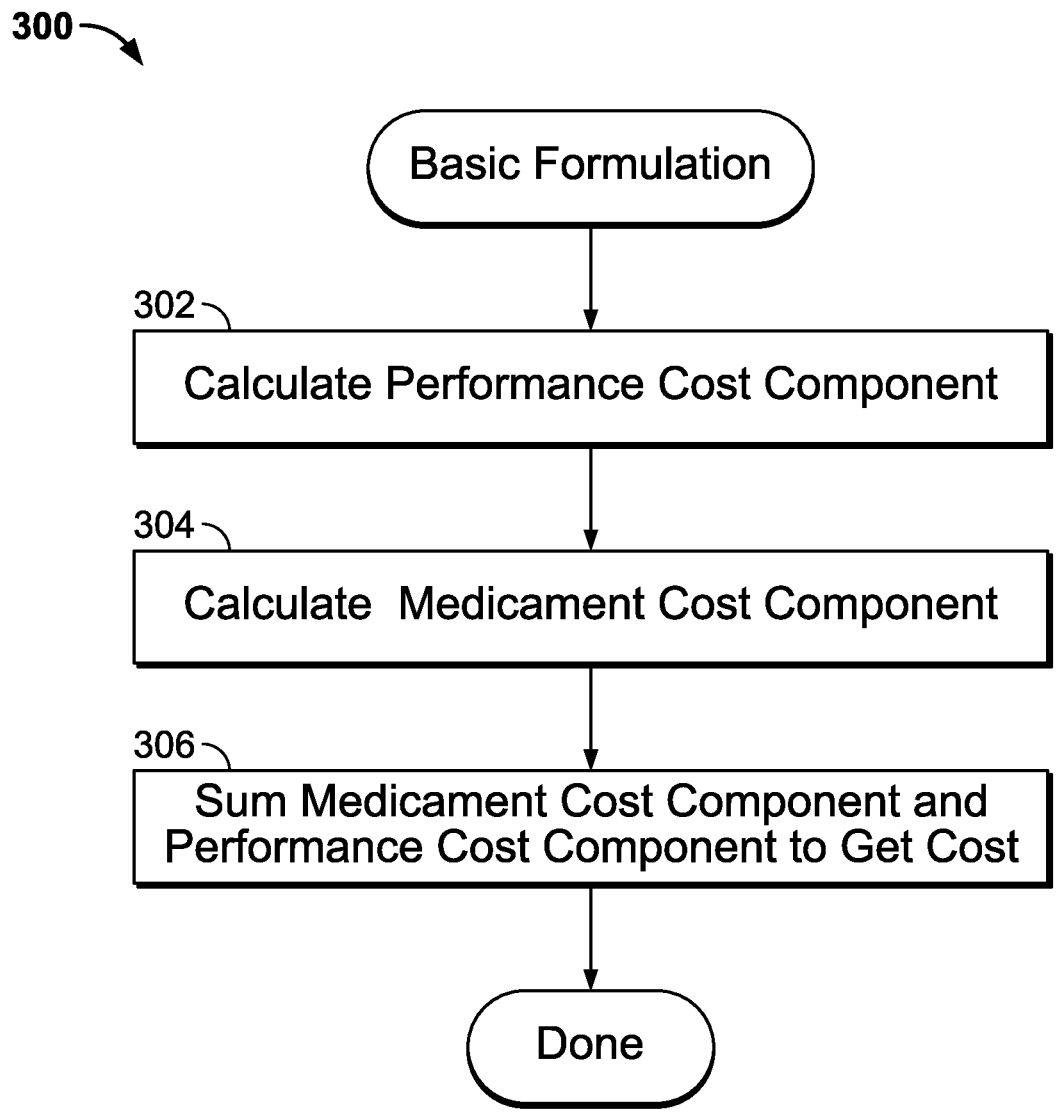
FIG. 3 depicts a flowchart of illustrative steps that may be performed to calculate a conventional cost function.

FIG. 3 depicts a flowchart 300 of illustrative steps that may be performed to calculate a cost function, such as that detailed in Equation 1. At 302, the medicament cost component is calculated. For this cost example conventional cost function, the performance cost component is the expression $Q \cdot \Sigma_{i=1}^{M} G_p(i)^2$, which is the glucose cost component. The performance cost component captures the cost in deviation from the target performance. For insulin delivery, the target performance is measured relative to a target blood glucose concentration. At 304, the medicament cost component is calculated. The medicament cost component captures the penalty of deviating from a reference medicament dosage, such as a standard basal dosage. In this conventional cost function, the medicament cost is the expression $R \cdot \Sigma_{i=1}^{n} I_p(i)^2$, which is the weighted insulin cost. At 306, the total cost J is calculated as the sum of the performance cost component and the medicament cost component.

Figure 4:
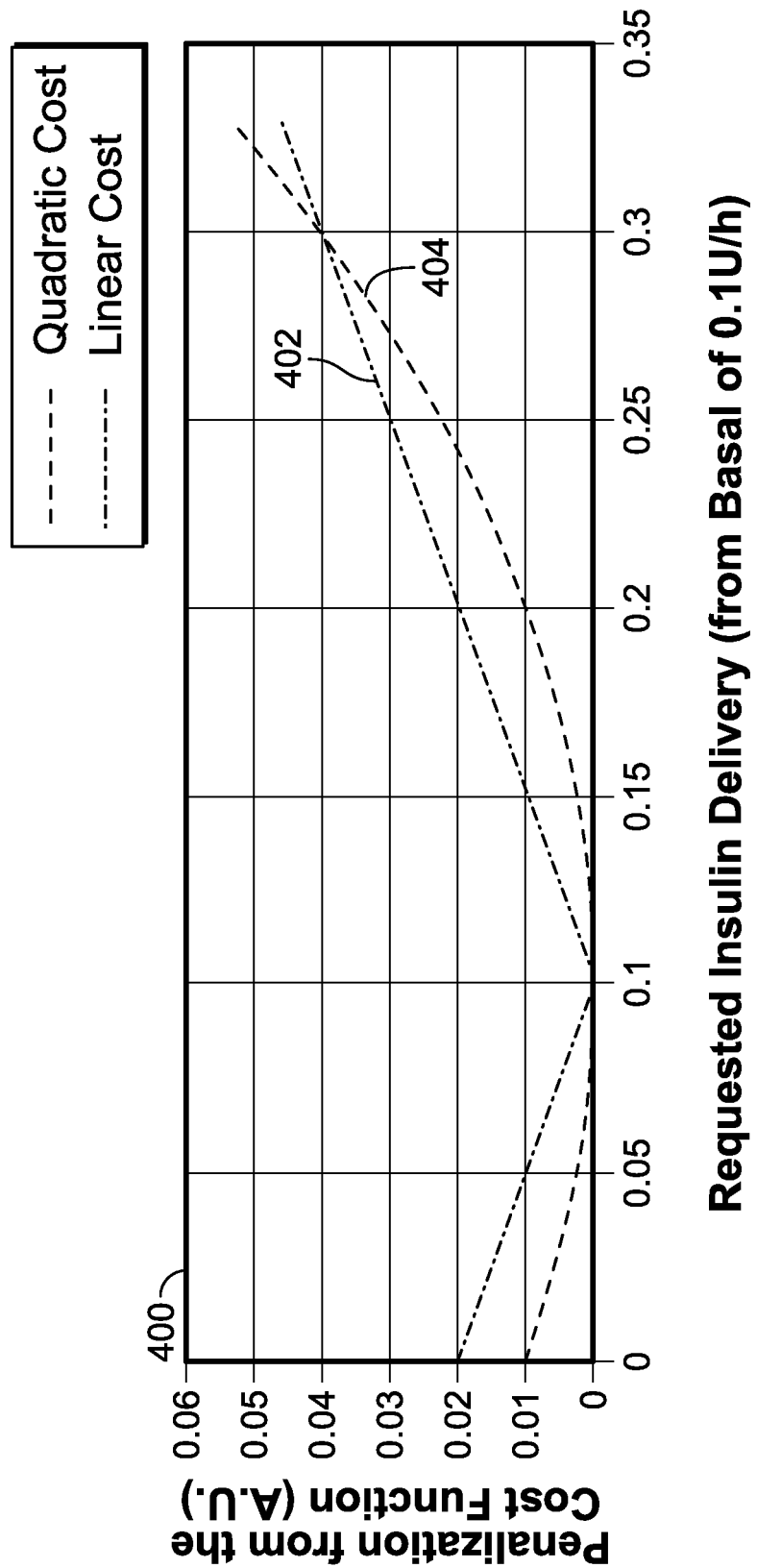
FIG. 4 depicts a plot of the value of the medicament cost component of a cost function versus requested dosage of medicament for a conventional linear medicament cost component and for a conventional quadratic medicament cost component.

Cost functions for conventional medicament delivery devices tend to specify the medicament cost function as a linear cost or a quadratic cost. In other words, the medicament cost function is expressed as a linear expression or as a quadratic expression. The conventional cost function described above has a quadratic medicament cost component since $R \cdot \Sigma_{i=1}^{n} I_p(i)^2$ is a quadratic expression. FIG. 4 depicts a plot 400 of the value of the medicament cost component of a cost function (see y-axis) versus a requested dosage of medicament (i.e., candidate dosage amount) for a linear medicament cost component and for a quadratic medicament cost component. The linear medicament cost component is represented by curve 402, and the quadratic medicament cost component is represented by curve 404 in the plot 400. The linear medicament cost component 402 has a linear formulation that scales in a linear fashion (i.e. along a line). The quadratic medicament cost component 404 has a quadratic formulation that scales quadratically. In the example of FIG. 4, the standard basal dosage is 0.1 units of insulin per hour. With the linear medicament cost component, the curve 402 shows that the penalty or cost decreases linearly from 0.02 (y-axis) when no insulin is requested to a zero penalty or cost for the medicament cost component at a requested dosage equal to the standard basal dosage. The penalty increases linearly for increasing dosages above or below the standard basal dosage such that the cost is symmetric about the standard basal dosage. For the quadratic medicament cost component, the penalty or cost starts at 0.01 (y-axis) when no insulin is requested and decreases in a quadratic fashion (i.e., parabolically) until a dosage equal to the standard basal dosage is reached. The penalty or cost increases in a quadratic fashion for dosages over the standard basal dosage such that the cost is symmetric about the standard basal dosage. The rate of increase of the penalty for the quadratic medicament cost component exceeds that of the linear medicament cost component for higher dosages such that, in this example, starting at a requested dosage of 0.3 U/h, the penalty for requested dosages with the quadratic medicament cost component exceeds that of the linear medicament cost component.

As can be seen from FIG. 4, with both the conventional linear medicament cost component and the conventional quadratic medicament cost component, there is a penalty for delivering insulin dosages below the standard basal dosage. The exemplary embodiments described below and in subsequent figures recognize that such a penalty may not be desirable. As was described above, such a penalty discourages delivering insulin dosages below a standard basal dosage. Thus, in accordance with some exemplary embodiments, the medicament cost component is zero or substantially zero (i.e., slightly more than zero but still negligible) for requested dosages below the standard basal dosage (i.e., the reference dosage mentioned above). This formulation of the medicament cost component allows the control system to be free to reduce medicament delivery as much as is needed to modify the predicted performance metric to the setpoint. This control approach can be more aggressive in reducing medicament delivery, while maintaining compensation for increases in medicament delivery relative to a standard basal dosage.

Figure 5:
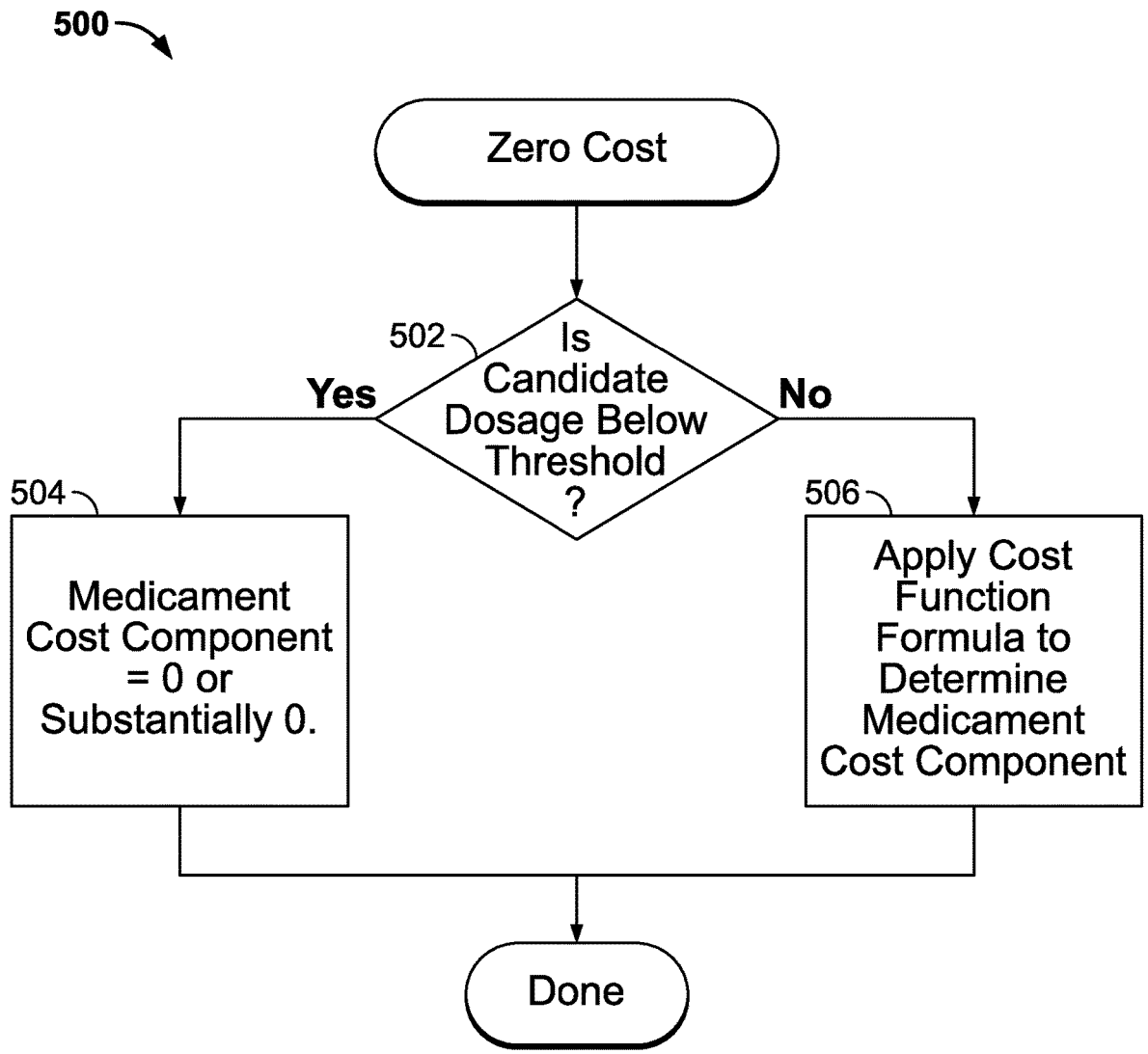
FIG. 5 depicts a flowchart of illustrative steps that may be performed in exemplary embodiments to realize the zero cost with the cost function.

FIG. 5 depicts a flowchart 500 of illustrative steps that may be performed in exemplary embodiments to realize a zero cost with the cost function. At 502, a check is made whether the candidate dosage is below a threshold, such as below a standard basal dosage. At 504, if the candidate dosage is below the threshold, the medicament cost component is set as zero or at a value that is substantially zero. At 506, if the candidate dosage is equal to or above the threshold, the medicament cost component is calculated using a formulation specified in the cost function.

An example formulation of a cost function that provides a zero-cost medicament cost component value below a threshold or standard basal dosage for insulin delivery is:

$$J = Q \cdot \sum_{i=1}^{M} G_p(i)^2 + R \cdot \sum_{i=1}^{n} I_p(i)^2 \text{ for } I_r > I_b \quad \text{(Equation 2.1)}$$

and $$J = Q \cdot \sum_{i=1}^{M} G_p(i)^2 \text{ for } I_r \leq I_b \quad \text{(Equation 2.2)}$$

where $I_r$ the requested dosage of insulin (i.e., a candidate dosage) and $I_b$ is basal dosage. Values substantially equal to 0 for the medicament cost component may be used instead of 0 in some exemplary embodiments.

The reference value that is used as a threshold below which the medicament cost component is zero or substantially zero may be a value other than the standard basal dosage. Sometimes, a user may have greater medicament needs than the standard basal formulation. As such, pegging deliveries at the standard basal dosage may not get rid of persistent low-level performance excursions above a blood glucose target. Therefore, some exemplary embodiments may set the threshold based on mean positive performance excursions above the blood glucose target. This enables the delivery of larger than standard basal dosages of medicament to reduce the positive performance excursions without penalty.

Figure 6:
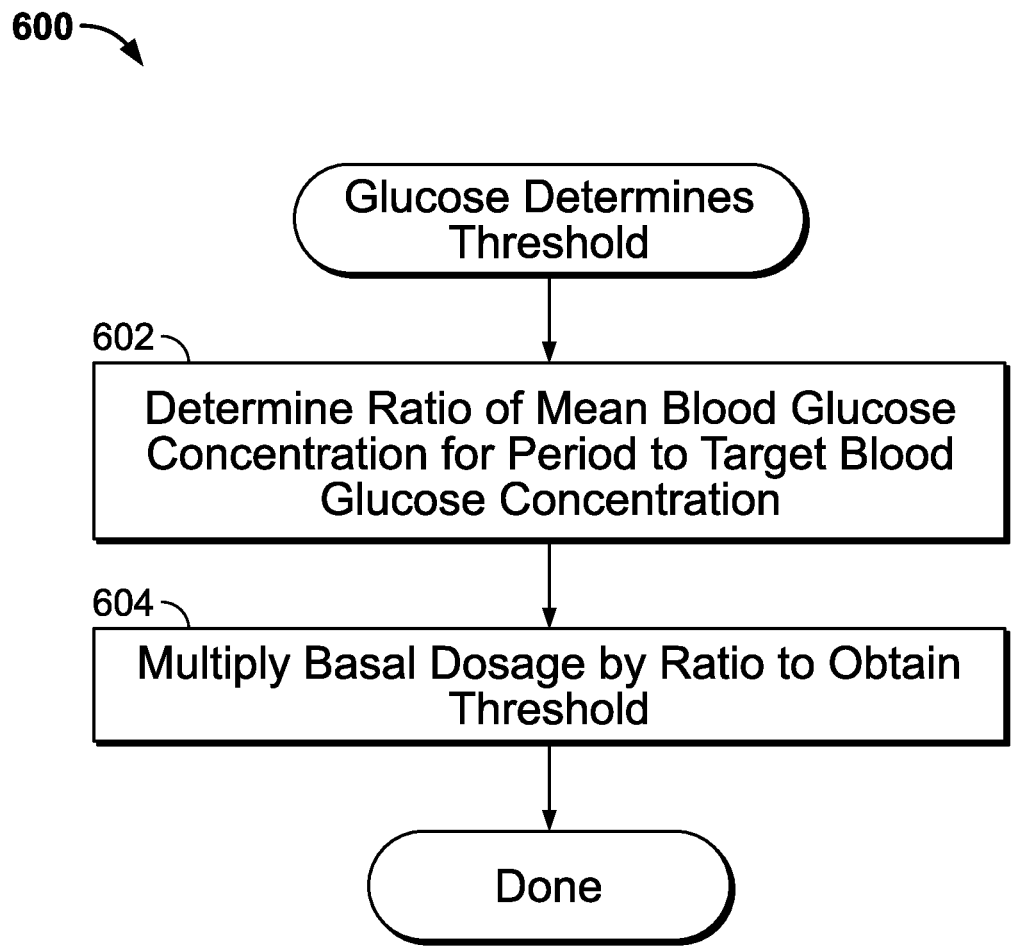
FIG. 6 depicts a flowchart of illustrative steps that may be performed to determine a threshold for a medicament cost component based on average blood glucose concentration of a user in exemplary embodiments.

One application of the threshold being adaptable higher than a standard basal dosage is for an insulin delivery device. In such an application, the threshold may be calculated as shown in the flowchart 600 of FIG. 6. At 602, a ratio of mean blood glucose concentration of a user for a period to target blood glucose concentration is calculated. This ratio reflects the degree to which a user's mean blood glucose concentration exceeds the target blood glucose concentration. At 604, the basal dosage is multiplied by the ratio to determine the threshold.

The cost function with the modified threshold base on mean glucose excursions may be expressed as:

$$J = Q \cdot \sum_{i=1}^{M} (G(i) - SP)^2 + R \cdot I_p(i) \quad \text{(Equation 3.1)}$$

$$I_p(i) = \sum_{i=1}^{n} (I_r^+(i) - I_b(i))^2 \quad \text{(Equation 3.2)}$$

$$I_r^+(i) = \begin{cases} I_r & I_r \geq \dfrac{G_{mean}}{G_t} \cdot I_b \\ I_b & I_r < \dfrac{G_{mean}}{G_t} \cdot I_b \end{cases} \quad \text{(Equation 3.4)}$$

$$G_{mean} = \dfrac{\sum_{j=1}^{12X} G(j)}{12X} \quad \text{(Equation 3.4)}$$

where $G_t$ is the mean blood glucose concentration target. The threshold is $$\dfrac{G_{mean}}{G_t} \cdot I_b.$$

Since the value of $I_r^+(i)$ is $I_b$ for values below the threshold, the insulin cost component $R \cdot I_p(i)$ is 0, since $I_p(i)$ is $I_b - I_b$ or 0.

Figure 7:
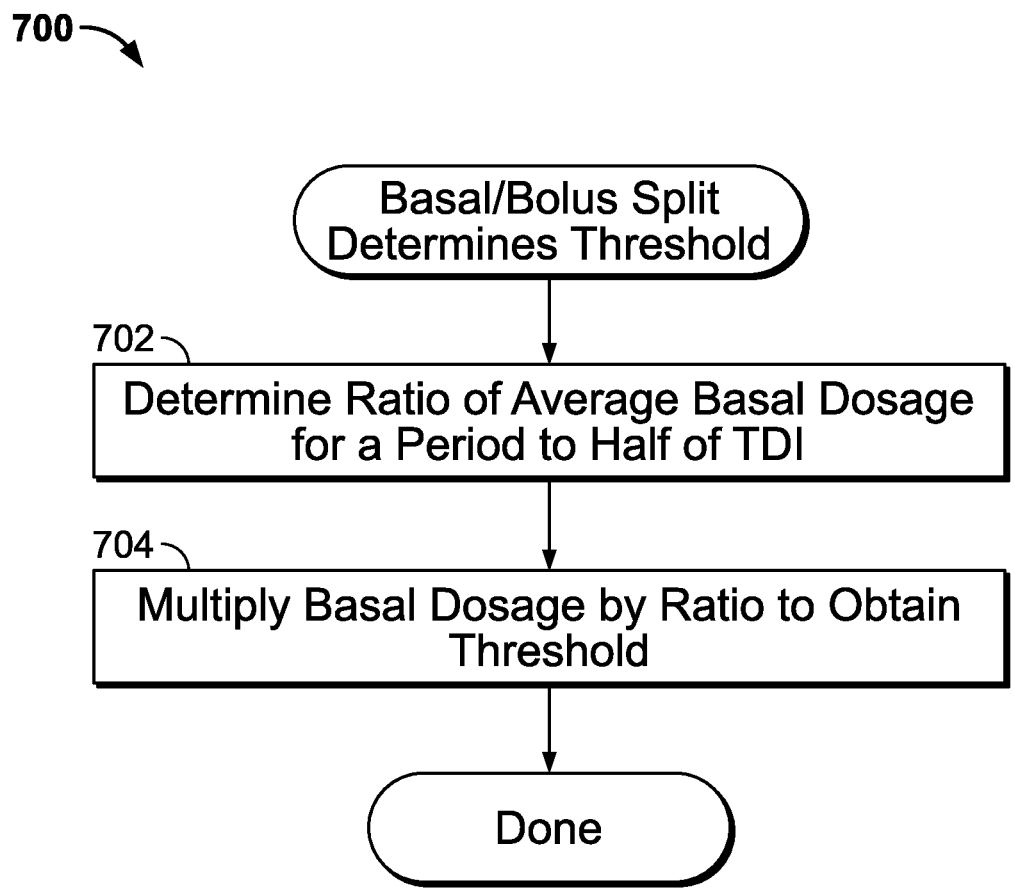
FIG. 7 depicts a flowchart of illustrative steps that may be performed to determine a threshold for a medicament cost component based on an actual ratio of average basal dosage for a user to total daily insulin (TDI) for the user in exemplary embodiments.

The threshold instead may be set based on a reference value of a user's actual basal/TDI split. Traditionally, the basal amount for a user is set at half of the user's TDI. Unfortunately, this rule of thumb does not work well for some users. To account for such users, the exemplary embodiments may determine the threshold based on the user's actual basal/TDI ratio. FIG. 7 depicts a flowchart 700 of steps that may be performed to determine such a threshold. At 702, the ratio of average basal dosage for a user over a period (e.g., daily) to half of the TDI for the user is determined. If the user has higher than normal insulin needs (i.e. greater than basal), the ratio will be greater than one. At 704, the standard basal dosage (i.e., 0.5 TDI) for the user is multiplied by the ratio to determine the threshold reference value. This enables the threshold to exceed the basal dosage where the average actual basal dosage is higher than the standard basal dosage.

The formulation of the cost function may be as described for the mean glucose excursions as described above, but $I_r^+(i)$ may be differently formulated as follows:

$$I_r^+(i) = \begin{cases} I_r & I_r \geq \max\left(1, \dfrac{I_{btotal}(t)}{0.5TDI}\right) \cdot I_b \\ I_b & I_r < \max\left(1, \dfrac{I_{btotal}(t)}{0.5TDI}\right) \cdot I_b \end{cases} \quad \text{(Equation 4.1)}$$

$$I_{btotal}(t) = 288 \dfrac{\sum_{j=1}^{12X} I_{bactual}(j)}{12X} \quad \text{(Equation 4.2)}$$

where $I_{btotal}$ is the total basal insulin over an interval and $I_{bactual}(i)$ is the actual basal insulin at cycle i.

Figure 8B:
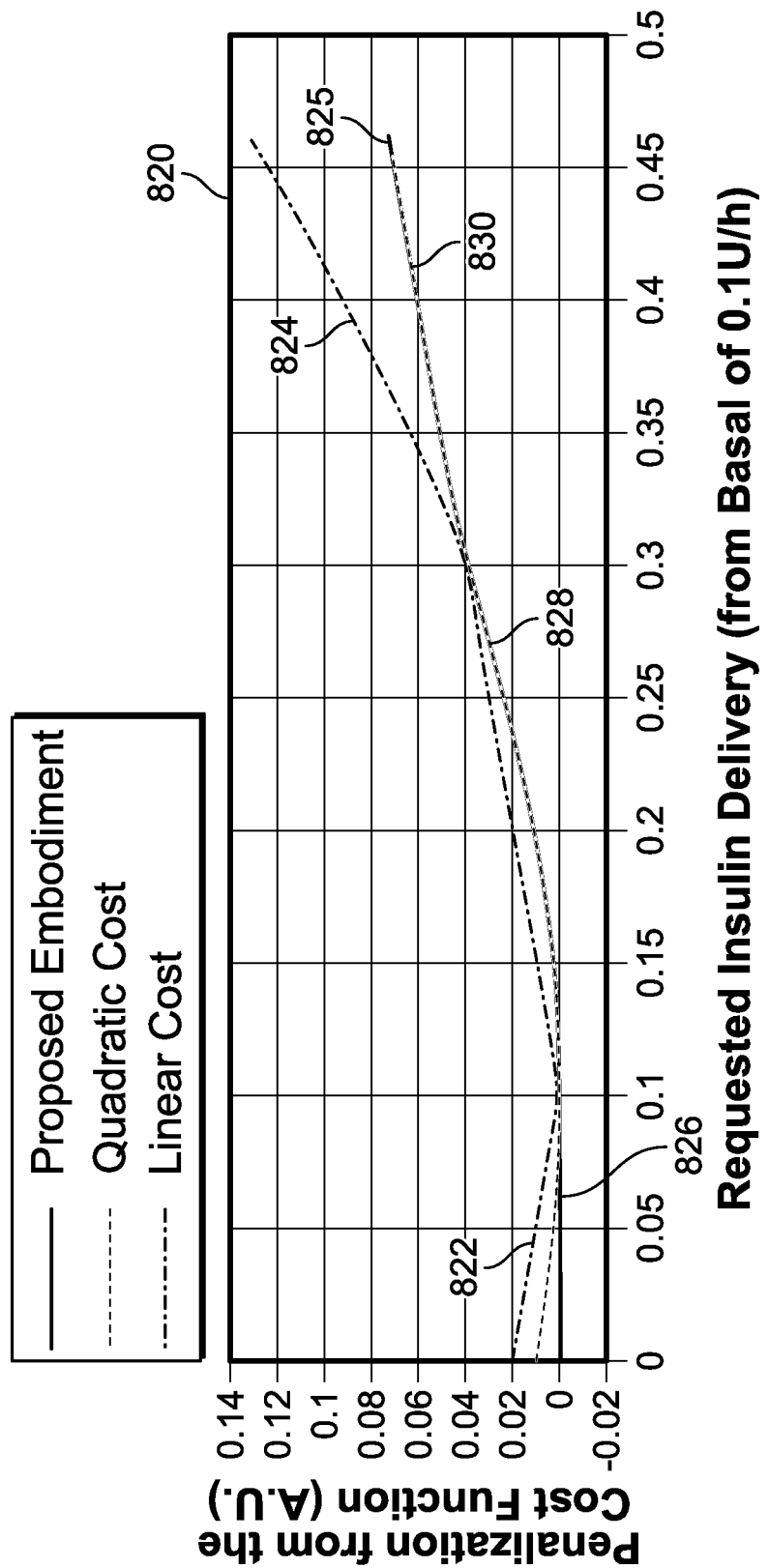
FIG. 8B depicts a plot illustrating mixed scaling across ranges of candidate medicament dosages for a medicament cost component in exemplary embodiments.

It may be desirable for a medicament cost component in a cost function to be asymmetric among different ranges to suit the medicament needs of the user. In other words, the medicament cost component may be differently scaled in different ranges. FIG. 8A depicts a flowchart 800 of an example where different scaling is used for different ranges of the medicament candidate dosages. In this example, at 802, the medicament cost component has a zero cost below a first threshold. An illustration of this is seen in plot 820 of FIG. 8B. The plot 820 shows curve 822, which has linear scaling, and curve 824 which has quadratic scaling like that depicted in FIG. 4. Curve 825 represents the medicament cost component over a range of candidate dosages, with scaling changing at different basal dosage rates. The region 826 of the curve before a requested insulin delivery of 0.1 U/h has a flat constant value of 0, such as was discussed above relative to FIG. 5. At 804, the scaling of the curve 825 changes to a quadratic scaling in region 828 that extends from 0.1 U/h to 0.3 U/h. This region 828 represents the range of requested dosages when the blood glucose concentration of the user is near target and the requested insulin dosage is slightly over the basal dosage. The quadratic scaling is well suited for this region 828, where insulin levels are elevated but not so large as to pose a threat to causing hypoglycemia. However, as the candidate dosage exceeds 0.3 U/h, the quadratic scaling may be too aggressive and may increase the risk of hypoglycemia. Thus, at 806, the scaling is reduced. Specifically, the insulin cost component has linear scaling when the requested insulin dosage is above a second threshold (e.g., 0.3 U/h) in region 830. This reduces the risk of hypoglycemia due to delivering too large of dosages of insulin.

Figure 9:
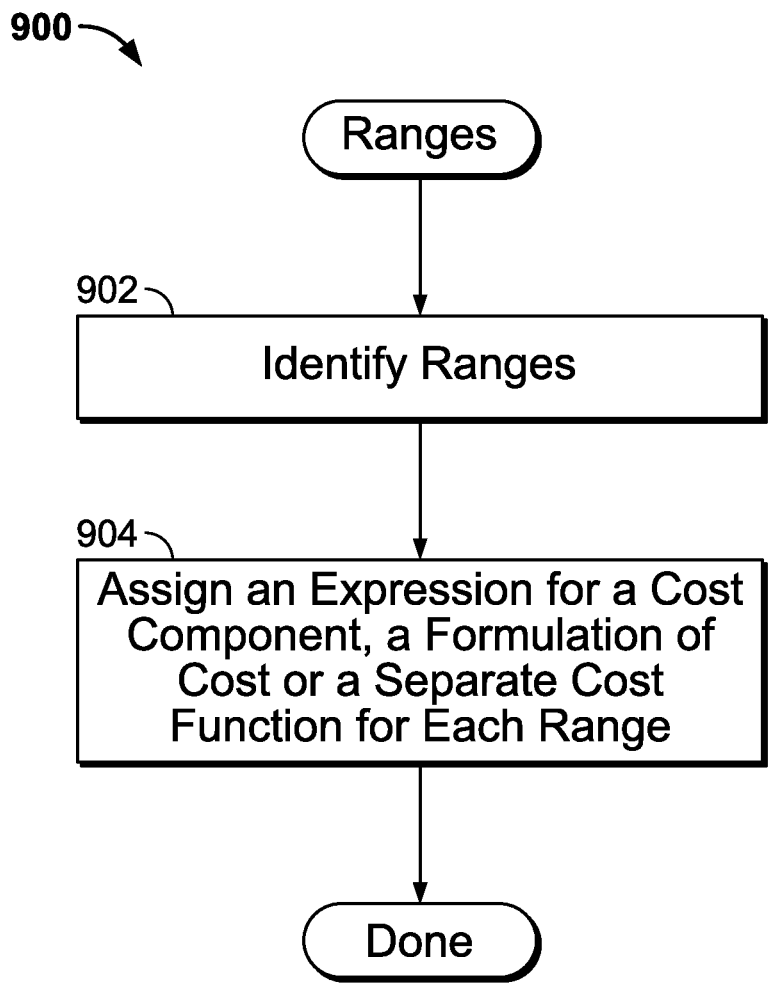
FIG. 9 depicts a flowchart of illustrative steps that may be performed as to provide asymmetry in a medicament cost component over ranges of candidate dosage in exemplary embodiments.

The above-described examples show that the medicament cost component and the cost function may be varied over different ranges of inputs (i.e., medicament dosages). It should be noted that more generally, the exemplary embodiments may use cost functions with asymmetry for the medicament cost components. FIG. 9 depicts a flowchart 900 of illustrative steps that may be performed as to provide asymmetry over the ranges. At 902, the ranges of candidate dosages of medicament are identified. At 904, an expression is assigned for a medicament cost component for each range, a formulation of the cost for each range is assigned, or a separate cost function is assigned for each range. This assignment provides the asymmetry over the ranges of candidate dosages. This asymmetry enables the control system to better customize the medicament cost components to a user's needs.

While the discussion herein has focused on exemplary embodiments, it should be appreciated that various change in form and detail may be made relative to the exemplary embodiments without departed from the intended scope of the claims appended hereto.

The invention claimed is:

1. A medicament delivery device, comprising:
a memory for storing data and computer programming instructions;
a pump for delivering a medicament to a user;
a processor for executing the computer programming instructions to:
determine values of a cost function for candidate dosages to the user, the cost function has a performance cost component and a medicament cost component,
wherein the medicament cost component is configured to be asymmetrical about a threshold amount; and
choose a dosage to be delivered to the user by the pump from among the candidate dosages based on values of the cost function for the candidate dosages.

2. The medicament delivery device of claim 1, wherein the threshold amount is an average basal dosage or a particular basal dosage for the user.

3. The medicament delivery device of claim 1, wherein the threshold amount is a multiple of a basal dosage amount for the user and the multiple is greater than one.

4. The medicament delivery device of claim 3, wherein the multiple is a ratio of mean blood glucose concentration over a time interval to target blood glucose concentration.

5. The medicament delivery device of claim 3, wherein the multiple is a ratio of average basal dosage delivered to the user over an interval to an estimate of basal dosage over the interval derived from total daily medicament for the user.

6. The medicament delivery device of claim 1, wherein choosing the dosage comprises choosing one of the candidate dosages with the lowest value for the cost function.

7. The medicament delivery device of claim 1, wherein the medicament delivery device delivers at least one of insulin, a glucagon-like peptide (GLP-1) agonist, or pramlintide.

8. The medicament delivery device of claim 1, wherein the medicament cost component is substantially zero for any of the candidate dosages below the threshold amount.

9. A medicament delivery device, comprising:
a memory for storing data and computer programming instructions;
a pump for delivering a medicament to a user;
a processor for executing the computer programming instructions to:
determine values of a cost function for candidate dosages of the medicament to the user, the cost function has a performance cost component and a medicament cost component,
wherein scaling of the medicament cost component is quadratic above a first threshold and linear above a second threshold that is greater than the first threshold; and
choose as a dosage to be delivered to the user by the pump among the candidate dosages to the user based on values of the cost function for the candidate dosages.

10. The medicament delivery device of claim 9, wherein the scaling of the medicament cost component is linear below the first threshold.

11. The medicament delivery device of claim 10, wherein the medicament cost component has a fixed value for at least one of the candidate dosages that is below the first threshold.

12. The medicament delivery device of claim 11, wherein the fixed value is zero or substantially zero.

13. A medicament delivery device, comprising:
a memory for storing data and computer programming instructions;
a pump for delivering a medicament to a user;
a processor for executing the computer programming instructions to:
determine values of a cost for candidate dosages to the user, the cost has a performance cost component and a medicament cost component;
wherein the cost is calculated in a different manner for different ranges of the candidate dosages; and
choose as a dosage to be delivered to the user by the pump among the candidate dosages to the user based on the values of the cost for the candidate dosages.

14. The medicament delivery device of claim 13, wherein the cost is calculated to be negligible for any ones of the candidate dosages in one of the ranges below a first threshold.

15. The medicament delivery device of claim 14, wherein the first threshold is an average basal dosage or a particular basal dosage for the user.

16. The medicament delivery device of claim 15, wherein the first threshold is a multiple of the average basal dosage or the particular basal dosage for the user and the multiple is greater than one.

17. The medicament delivery device of claim 14, wherein the cost includes a medicament cost component that is calculated by a quadratic formulation in a one of the ranges above a second threshold that is greater than the first threshold.

18. The medicament delivery device of claim 17, wherein the cost includes a medicament cost component that is calculated by a linear formulation in a one of the ranges above a third threshold that is greater than the second threshold.

19. The insulin delivery device of claim 13, wherein the cost is calculated using a cost function and the cost function scales differently in at least two of the ranges.

20. The insulin delivery device of claim 19, wherein the cost function includes a performance cost component and an medicament cost component and the medicament cost component differs in the at least two of the ranges to cause the medicament cost component to scale differently in the at least two of the ranges.

21. The insulin delivery device of claim 19, wherein the cost function has a medicament cost component and the cost is determined for a first of ranges using a different formula for medicament cost than used in determining the cost for a second of the ranges.

22. The insulin delivery device of claim 13, wherein the cost is determined by a different cost function for each range.

23. The medicament delivery device of claim 13, wherein the medicament is one of insulin, a glucagon-like peptide-1 (GLP-1) agonist, or pramlintide.

* * * * *